United States Patent
Deffenbaugh et al.

(10) Patent No.: US 7,922,769 B2
(45) Date of Patent: Apr. 12, 2011

(54) MODULAR GLENOID PROSTHESIS AND ASSOCIATED METHOD

(75) Inventors: Daren Lloyd Deffenbaugh, Winona Lake, IN (US); Thomas Scott Camino, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/951,021

(22) Filed: Sep. 27, 2004

(65) Prior Publication Data

US 2006/0069443 A1 Mar. 30, 2006

(51) Int. Cl.
 *A61F 2/40* (2006.01)
(52) U.S. Cl. ..................................................... 623/19.11
(58) Field of Classification Search .... 623/19.11–19.14, 623/22.21–22.39
See application file for complete search history.

(56) References Cited

U.S. PATENT DOCUMENTS

| | | | |
|---|---|---|---|
| 3,837,008 A | 9/1974 | Bahler et al. | |
| 3,855,638 A | 12/1974 | Pilliar | |
| 4,040,130 A | 8/1977 | Laure | |
| 4,106,128 A | 8/1978 | Greenwald et al. | |
| 4,172,296 A | 10/1979 | D'Errico | |
| 4,180,871 A | 1/1980 | Hamas | |
| 4,550,450 A | 11/1985 | Kinnett | |
| D285,968 S * | 9/1986 | Kinnett | D24/155 |
| 4,693,723 A * | 9/1987 | Gabard | 623/19.12 |
| 4,695,282 A * | 9/1987 | Forte et al. | 623/22.29 |
| 4,865,025 A | 9/1989 | Buzzi et al. | |
| 4,865,605 A | 9/1989 | Dines et al. | |
| 4,919,670 A * | 4/1990 | Dale et al. | 623/19.14 |
| 4,936,853 A | 6/1990 | Fabian et al. | |
| 4,964,865 A | 10/1990 | Burkhead et al. | |
| 4,987,904 A | 1/1991 | Wilson | |
| 5,030,219 A | 7/1991 | Matsen, III | |
| 5,047,058 A | 9/1991 | Roberts et al. | |
| 5,108,446 A * | 4/1992 | Wagner et al. | 623/22.28 |
| 5,197,465 A | 3/1993 | Montgomery | |
| 5,201,882 A | 4/1993 | Paxson | |
| 5,304,181 A | 4/1994 | Caspari et al. | |
| 5,314,479 A | 5/1994 | Rockwood et al. | |
| 5,344,461 A | 9/1994 | Phlipot | |
| 5,358,526 A | 10/1994 | Tornier | |
| 5,370,693 A | 12/1994 | Kelman et al. | |
| 5,387,241 A | 2/1995 | Hayes | |
| 5,437,677 A | 8/1995 | Shearer et al. | |
| 5,458,637 A | 10/1995 | Hayes | |
| 5,474,559 A | 12/1995 | Bertin et al. | |
| 5,486,180 A | 1/1996 | Dietz et al. | |
| 5,489,309 A | 2/1996 | Lackey et al. | |
| 5,489,310 A * | 2/1996 | Mikhail | 623/19.11 |

(Continued)

FOREIGN PATENT DOCUMENTS

EP 01/03246 A1 3/1984

(Continued)

*Primary Examiner* — Thomas C Barrett
*Assistant Examiner* — Nicholas Woodall

(57) ABSTRACT

A glenoid implant assembly is provided. The assembly includes a first component for attachment to the glenoid fossa of a scapula. The component defines an assembly face of the component. The assembly also includes a second component removably secured to the first component. The second component includes an assembly face of the second component. The assembly face of the second component is in close approximation to the assembly face of the first component. The second component is attachable to the first component in a direction generally normal to the assembly faces.

25 Claims, 18 Drawing Sheets

U.S. PATENT DOCUMENTS

| | | | |
|---|---|---|---|
| 5,496,324 A | 3/1996 | Barnes | |
| 5,507,821 A | 4/1996 | Sennwald et al. | |
| 5,554,158 A | 9/1996 | Vinciguerra et al. | |
| 5,593,441 A | 1/1997 | Lichtenstein et al. | |
| 5,593,448 A | 1/1997 | Dong | |
| 5,601,563 A | 2/1997 | Burke et al. | |
| 5,665,090 A | 9/1997 | Rockwood et al. | |
| 5,718,360 A | 2/1998 | Green et al. | |
| 5,723,018 A | 3/1998 | Cyprien et al. | |
| 5,743,915 A | 4/1998 | Bertin et al. | |
| 5,769,855 A | 6/1998 | Bertin et al. | |
| 5,779,710 A | 7/1998 | Matsen | |
| 5,782,924 A | 7/1998 | Johnson | |
| 5,800,551 A | 9/1998 | Williamson et al. | |
| 5,853,415 A | 12/1998 | Bertin et al. | |
| 5,860,981 A | 1/1999 | Bertin et al. | |
| 5,879,401 A * | 3/1999 | Besemer et al. | 623/22.28 |
| 5,908,424 A | 6/1999 | Bertin et al. | |
| 5,928,285 A | 7/1999 | Bigliani et al. | |
| 5,976,145 A | 11/1999 | Kennfick, III | |
| 6,045,582 A | 4/2000 | Prybyla | |
| 6,096,084 A | 8/2000 | Townley | |
| 6,139,581 A | 10/2000 | Engh et al. | |
| 6,197,062 B1 | 3/2001 | Fenlin | |
| 6,197,063 B1 | 3/2001 | Dews | |
| 6,206,925 B1 * | 3/2001 | Tornier | 623/19.12 |
| 6,228,119 B1 | 5/2001 | Ondrla et al. | |
| 6,228,900 B1 | 5/2001 | Shen et al. | |
| 6,245,074 B1 | 6/2001 | Allard et al. | |
| 6,281,264 B1 | 8/2001 | Salovey et al. | |
| 6,364,910 B1 | 4/2002 | Shultz et al. | |
| 6,368,353 B1 | 4/2002 | Arcand | |
| 6,379,386 B1 | 4/2002 | Resch et al. | |
| 6,406,495 B1 | 6/2002 | Schoch | |
| 6,514,287 B2 | 2/2003 | Ondrla et al. | |
| 6,620,197 B2 | 9/2003 | Maroney et al. | |
| 6,676,705 B1 | 1/2004 | Wolf | |
| 6,679,916 B1 | 1/2004 | Frankle et al. | |
| 6,699,289 B2 | 3/2004 | Iannotti et al. | |
| 6,893,702 B2 | 5/2005 | Takahashi | |
| 6,896,702 B2 | 5/2005 | Collazo | |
| 6,899,736 B1 | 5/2005 | Rauscher et al. | |
| 6,942,699 B2 * | 9/2005 | Stone et al. | 623/19.14 |
| 7,051,451 B2 | 5/2006 | Augostino et al. | |
| 7,090,677 B2 | 8/2006 | Fallin et al. | |
| 7,160,331 B2 | 1/2007 | Cooney et al. | |
| 7,175,665 B2 | 2/2007 | German et al. | |
| 7,527,631 B2 | 5/2009 | Maroney et al. | |
| 7,604,665 B2 | 10/2009 | Iannotti et al. | |
| 7,608,109 B2 | 10/2009 | Pria | |
| 7,625,408 B2 | 12/2009 | Gupta et al. | |
| 7,766,969 B2 | 8/2010 | Justin et al. | |
| 2001/0011192 A1 | 8/2001 | Ondrla et al. | |
| 2001/0018589 A1 | 8/2001 | Muller | |
| 2001/0030339 A1 | 10/2001 | Sandhu et al. | |
| 2002/0082702 A1 | 6/2002 | Resch et al. | |
| 2002/0099445 A1 | 7/2002 | Maroney et al. | |
| 2003/0028253 A1 * | 2/2003 | Stone et al. | 623/19.14 |
| 2003/0045883 A1 | 3/2003 | Chow et al. | |
| 2003/0055507 A1 * | 3/2003 | McDevitt et al. | 623/19.11 |
| 2003/0065397 A1 | 4/2003 | Hanssen et al. | |
| 2003/0097183 A1 | 5/2003 | Rauscher et al. | |
| 2003/0114933 A1 | 6/2003 | Bouttens et al. | |
| 2003/0149485 A1 | 8/2003 | Tornier | |
| 2003/0187514 A1 | 10/2003 | McMinn | |
| 2004/0064189 A1 | 4/2004 | Maroney et al. | |
| 2004/0162619 A1 | 8/2004 | Blaylock et al. | |
| 2004/0193277 A1 | 9/2004 | Long et al. | |
| 2004/0193278 A1 * | 9/2004 | Maroney et al. | 623/19.14 |
| 2004/0220673 A1 * | 11/2004 | Pria | 623/19.12 |
| 2004/0220674 A1 * | 11/2004 | Pria | 623/19.12 |
| 2004/0230312 A1 | 11/2004 | Hanson et al. | |
| 2005/0021148 A1 | 1/2005 | Gibbs | |
| 2005/0125068 A1 | 6/2005 | Hozack et al. | |
| 2005/0171613 A1 | 8/2005 | Sartorius et al. | |
| 2006/0030946 A1 | 2/2006 | Ball et al. | |
| 2006/0069443 A1 | 3/2006 | Deffenbaugh et al. | |
| 2006/0069444 A1 | 3/2006 | Deffenbaugh | |
| 2006/0074353 A1 | 4/2006 | Deffenbaugh et al. | |
| 2006/0074430 A1 | 4/2006 | Deffenbaugh et al. | |
| 2006/0100714 A1 | 5/2006 | Ensign | |
| 2006/0161260 A1 | 7/2006 | Thomas et al. | |
| 2007/0219637 A1 | 9/2007 | Berelsman et al. | |
| 2007/0219638 A1 | 9/2007 | Jones et al. | |
| 2007/0225817 A1 | 9/2007 | Reubelt et al. | |
| 2008/0208348 A1 | 8/2008 | Fitz | |
| 2008/0234820 A1 | 9/2008 | Felt et al. | |
| 2009/0125113 A1 | 5/2009 | Guederian et al. | |
| 2009/0143865 A1 | 6/2009 | Hassler et al. | |
| 2009/0204225 A1 | 8/2009 | Meridew et al. | |
| 2009/0281630 A1 | 11/2009 | Delince et al. | |

FOREIGN PATENT DOCUMENTS

| | | |
|---|---|---|
| EP | 0 339 530 A2 | 11/1989 |
| EP | 03/29854 B1 | 11/1992 |
| EP | 05/38895 A2 | 4/1993 |
| EP | 05/38895 A3 | 4/1993 |
| FR | 2652498 A1 | 4/1991 |
| FR | 2704747 A | 11/1994 |
| FR | 2776506 A | 10/1999 |
| WO | 01/34040 A1 | 5/2001 |
| WO | WO 02/067821 A3 | 6/2002 |
| WO | WO 02/067821 A2 | 9/2002 |
| WO | WO 03/005933 A2 | 1/2003 |
| WO | WO 03/005933 A3 | 1/2003 |
| WO | WO 03/030770 A2 | 4/2003 |

* cited by examiner

MODULAR GLENOID PROSTHESIS AND ASSOCIATED METHOD

TECHNICAL FIELD OF THE INVENTION

The present invention relates generally to the field of orthopaedics, and more particularly, to an implant for use in arthroplasty.

CROSS-REFERENCE TO RELATED APPLICATIONS

Cross reference is made to the following applications: U.S. patent application Ser. No. 10/951,023, which has now been abandoned, entitled "EXTENDED ARTICULATION PROSTHESIS ADAPTOR AND ASSOCIATED METHOD", U.S. patent application Ser. No. 10/951,024 entitled "GLENOID AUGMENT AND ASSOCIATED METHOD", U.S. patent application Ser. No. 10/950,615 entitled "INSTRUMENT FOR PREPARING AN IMPLANT SUPPORT SURFACE AND ASSOCIATED METHOD", and U.S. patent application Ser. No. 10/951,022 entitled "GLENOID INSTRUMENTATION AND ASSOCIATED METHOD", filed concurrently herewith which are incorporated herein by reference.

BACKGROUND OF THE INVENTION

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component typically has an elongated intramedullary stem which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

As alluded to above, the need for a shoulder replacement procedure may be created by the presence of any one of a number of conditions. One such condition is the deterioration of the patient's scapula in the area proximate to the glenoid surface as a result of, for example, glenohumeral arthritis. In such a condition, the erosion of the patient's scapula is generally observed posteriorly on the glenoid surface. Such erosion of the scapula renders treatment difficult, if not impossible, with a conventional glenoid prosthesis.

Referring now to FIG. 4 a prior art glenoid implant 1 is shown. Implant 1 includes a metal body to which a polyethylene glenoid bearing 3 is attached. A plurality of screws are used to secure the metal body to the glenoid. A central peg 5 may also be used to assist in securing the implant 1 to the glenoid.

Referring now to FIG. 3 a prior art glenoid bearing is shown as plastic glenoid bearing 6. The plastic glenoid bearing 6 includes a body 7 from which a plurality of pegs 8 extend. The plastic glenoid bearing 6 may also include a central peg 9, which likewise extends from the body 7 of the plastic glenoid bearing 6.

Referring now to FIG. 4, a prior art glenoid bearing is shown as metal backed glenoid bearing 1. The metal backed glenoid 1 includes a metal backing 2 and a plastic bearing 3. Screws 4 are used to secure the metal backing 2. A central post 5 may also be used to secure the metal backing 2.

Total shoulder replacement surgery includes the replacement of the humeral component and the glenoid component. The glenoid component is often the cause for a need of a revision. The need of a revision for a glenoid component is often due to the loosening of the glenoid component. Although there are many potential causes for loosening, there are no adequate solutions to the problem.

Polyethylene glenoids may wear and the polyethylene wear may lead to osteolysis and to aseptic wear loosening. Glenoid components have been provided which include a metal backing for fixation to the scapula and traditional snapped-in polyethylene components secured to the metal backed glenoid. These metal backed glenoids get better fixation, but tend to fail by polyethylene component disassociation from the metal backing. For a glenoid to be successful, the implant must be well fixed and the polyethylene must not disassociate itself from other components such as its metal backing.

The present invention is adapted to overcome at least some of the afore mentioned problems.

SUMMARY OF THE INVENTION

The present invention relates to a glenoid component for a shoulder prosthesis. The glenoid component is designed to have a portion that is used as a removable articular component, which is a standard component to be used with a total shoulder replacement system. The removable articular component may be selectively utilized with any of several fixation components. The components may be selected relative to specific applications for which they are intended. A fixation component of the glenoid prosthesis had a surface which interfaces with the supporting bony structure. The fixation components may be shaped relative to the specific condition.

The removable articular bearing component may have a composite structure including a molded metal back poly-bearing surface. The removable articular bearing component may engage the metal fixation component via a simple selectively releasable locking means. Such a selectively releasable locking means may be in the form for example a taper fit, for example a Morse taper.

Alternatively, the removable articulating bearing component may be replaced with a spherically convex component for use in reverse shoulder arthroplasty. This reverse shoulder spherical component may be reversibly locked to any of the fixation components. The invention may permit a surgeon to implant a traditional anatomic prosthesis and later convert the traditional total shoulder replacement with a reverse shoulder if the patient's condition warrants it.

According to the present invention a modular glenoid prosthesis for the use in total shoulder replacement surgery is provided. The modular glenoid prosthesis includes a replaceable molded backed polyethylene component that can be reversibly locked into a metal fixation component. The metal fixation component may be of a standard type or may be designed to treat a more pathologic shoulder condition such as a posteriorly eroded glenoids or glenoids with other large bony defects.

The metal fixation component may have a feature, such as a taper, for example a Morse taper, for reversibly locking the metal fixation component to the polyethylene component. The locking feature may additionally be used with a convex spherical component for use with reverse shoulder prosthesis permitting a surgeon to implant a traditional anatomic implant and then later, as the patient's conditions warrant, convert the total shoulder arthroplasty to a reverse prosthesis or vice versa.

The articulating surface of the modular glenoid component of the present invention may be made of a polyethylene, for example an ultra-high molecular weight polyethylene, and may be made of a cross-linked polyethylene. The cross-linked, ultra-high, molecular weight polyethylene should provide decreased wear and thus permit a thinner glenoid be used. The polyethylene may be molded to a porous coated spherical surface and the porous coating may be, for example, sintered to a thin metal substrate. The substrate may have a feature on the opposite side of the porous coating designed for locking the component to mating feature on a metal fixation component. The metal fixation component and the metal backed polyethylene component provide an example of a molded metal backed poly-bearing component according to the present invention.

The bearing component of the present invention may be in the form of other embodiments that may include alternative materials such as metal or ceramic for the articulating surface. The metal fixation component may have a spherically shaped surface that conforms to the convex spherical shape of the polyethylene molded metal backed component. The fixation component may have a finite thickness and the opposite side of the component, the side that will interface with the bony surface of the scapula, may be porous coated for enhanced fixation. Screw holes may be positioned in the fixation component to permit good internal fixation. The bony interfacial surface may be conjured to fit several glenoid shapes. These shapes include glenoids that exhibit posterior erosion or other large defects. The metal fixation component may be porous coated or include other biologic factors to stimulate bone growth on the interfacial surface for enhanced fixation.

According to one embodiment of the present invention, there is provided a glenoid implant assembly. The assembly includes a first component for attachment to the glenoid fossa of a scapula. The component defines an assembly face of the component. The assembly also includes a second component removably secured to the first component. The second component includes an assembly face of the second component. The assembly face of the second component is in close approximation to the assembly face of the first component. The second component is attachable to the first component in a direction generally normal to the assembly faces.

According to another embodiment of the present invention there is provided a glenoid implant assembly. The glenoid implant assembly includes a first component for attachment to the glenoid fossa of a scapula. The first component defines an assembly face and attachment feature of the first component. The glenoid implant assembly also includes a second component removably secured to the first component. The second component includes an assembly face of the second component. The second component defines an attachment feature of the second component. The attachment feature of the second component adapted for attaching to the attachment feature of said first component in a direction generally normal to the assembly faces.

According to a further embodiment of the present invention, there is provided a method for performing arthroplasty on a glenoid fossa of a scapula. The method includes the steps of providing a first glenoid component for attachment to the glenoid and attaching the first glenoid component to the glenoid. The method also includes the steps of providing a second glenoid component for attachment to the first glenoid component and attaching the second glenoid component to the first glenoid component in a direction generally normal to the longitudinal axis of the first glenoid component.

The technical advantages of the present invention include the ability to reduce problems with aseptic loosening of the glenoid. For example, according to one aspect of the present invention, a glenoid implant assembly is provided including a first component for attachment to the glenoid fossa of a scapula and a second component removably secured to the first component the second component is attachable to the first component in a direction generally normal to the assembly faces of the components. The portion of the first component for attachment to the glenoid fossa may include a surface, which assists in the prevention of the aseptic loosening of the glenoid. Thus the present invention provides for a reduction in the problem of aseptic loosening of glenoids.

The technical advantage of the present invention further include the ability of the present invention to reduce problems with the polyethylene bearing coming off the metal support. For example, according one aspect of the present invention, a glenoid implant assembly is provided including a first component for attachment to the glenoid fossa and a second component firmly secured to the first component. The second component is attached to the first component in a direction generally normal to the assembly faces of the first component and the second component. The polyethylene may be secured to the second component. The second component may include a feature on the context surface of the second component that engages the polyethylene to reduce the incidence of the polyethylene coming off of the second component. For example, the second component may include a porous or contoured surface with which the polyethylene may be inferenceably molded there to. Thus, the present invention provides for a reduction in the problems with the polyethylene component coming off of the metal support of the glenoid implant assembly.

The technical advantages of the present invention also include the replacement of the polyethylene without removal of the bone fixation of the glenoid component. For example, according to one aspect of the present invention, a glenoid component implant assembly is provided including a first component for attachment to the glenoid fossa and a second component removably secured to the first component. The second component is attachable to the first component in a direction generally normal to the assembly faces. The second component may include the polyethylene bearing connected to the second component. The second component including the polyethylene bearing may be removed from the second component and a second or replacement second component may be secured to the first component without removal of the bone fixation of the first component to the glenoid fossa of the scapula. Thus the present invention provides for the replacement of the polyethylene bearing without removal of the bone fixation of the glenoid implant assembly.

The technical advantages of the present invention include the ability of the glenoid implant assembly of the present invention to permit conversion to a reverse shoulder prosthesis. For example, according to one aspect of the present invention a glenoid implant assembly is provided including a first component for attachment to the glenoid fossa and a second component removably secured to the first component. The second component may be designed for a standard prosthesis. An alternative second component which is design for use with a reverse prosthesis may be replaced with the second component. Thus the present invention provides for the conversion of a glenoid implant assembly from a standard prosthesis to a reverse prosthesis.

The technical advantages of the present invention include the ability of the glenoid implant assembly of the present invention to provide for a wide range of prostheses utilizing a limited number of components. For example, according to one aspect of the present invention a glenoid implant kit is provided which includes a plurality of first components for attachment to the glenoid fossa and a plurality of components for attachment to the second components. Each of the plurality of first components cooperate with each of the second components so that many combinations of prostheses may be had from a limited number of components. Thus the present invention provides for a wide variety of implant offerings with the benefit of part reduction.

The technical advantages of the present invention further include the ability to provide prosthetic components with improved materials without removal of the bone fixation of the glenoid implant assembly. For example, according to one aspect of the present invention a glenoid implant assembly is provided including a first component for attachment to the scapula and a second component removably attached to the first component. The second component may include a bearing surface which may be initially made of, for example, a polyethylene and may later replaced with a different, second component made of a different material, for example, a ceramics or a metal. Thus the present invention provides for replacement of the original articulating bearing material with a alternate material without removal of the bone fixation of the glenoid assembly.

The technical advantages of the present invention further includes the ability to provide for superior fixation of the glenoid assembly by providing for many cross-holes in the implant assembly for use with a corresponding number of screws. For example, according to one aspect of the present invention a glenoid implant assembly is provided including a first component for attachment to the scapula. The first component may include a large number of cross-holes. A second component is removeably securable to the first component. Thus the present invention provides for a glenoid implant assembly which includes may cross-holes.

The technical advantages of the present invention further include the ability to use the glenoid implant assembly with vault fixation. For example, according to one aspect of the present invention a glenoid implant assembly is provided including a first component for attachment to the glenoid fossa of the scapula. The first component includes a feature for securement to the glenoid vault. A second component is removeably secured to the first component. Thus the present invention provides for a glenoid implant assembly that can be used with vault fixation.

The technical advantages of the present invention further include the ability to use the glenoid implant assembly of the present invention to correct defective glenoids with posterior erosion. For example, according to another aspect of the present invention a glenoid implant assembly is provided including a first component for attachment to the glenoid fossa of a scapula. The first component includes an augmentation or an additional portion for compensating for a void in the scapula. The glenoid implant assembly further includes a second component removeably secured to the first component. Thus the present invention provides for a glenoid implant assembly that can be used with posterior erosion.

Other technical advantages of the present invention will be readily apparent to one skilled in the art from the following FIGS., descriptions and claims.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
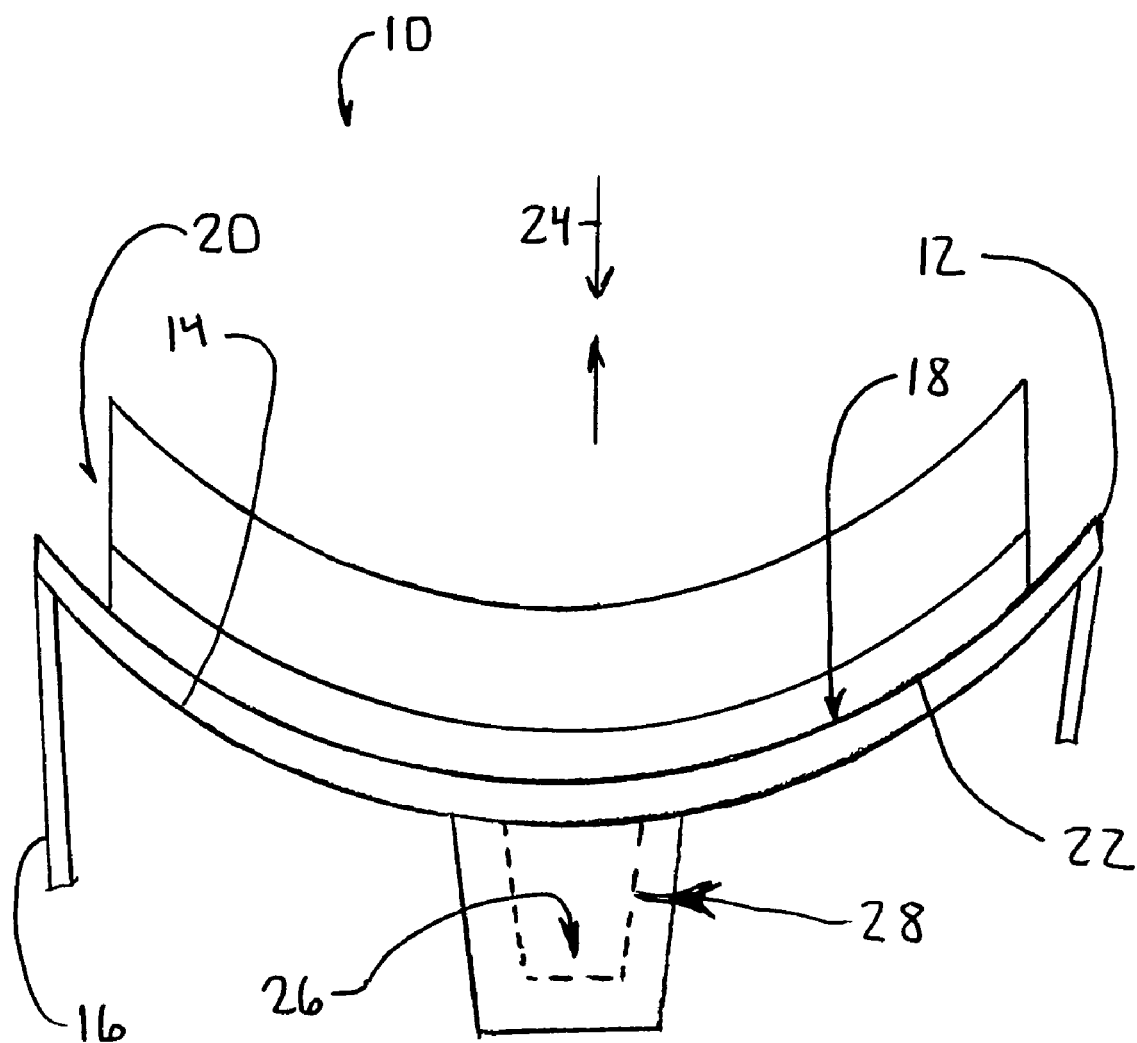
FIG. 1 is a plan view partially in cross-section of a metal backed plastic articulating modular glenoid assembly with a tapered connection and a concave articulating surface according to an embodiment of the present invention.

According to the present invention and referring now to FIG. 1 a glenoid implant assembly 10 is shown. The glenoid implant assembly 10 includes a first component 12 for attachment to the glenoid fossa 14 of a scapula 16. First component 12 defines an assembly face 18.

The glenoid implant assembly 10 further includes a second component 20. The second component 20 as shown in FIG. 1 is removeably secured to the first component 12. The second component 20 includes an assembly face 22. The assembly face 22 of the second component 20 is in close approximation to the assembly face 18 of the first component 12. The second component 20 is attachable to the first component 12 in the direction of arrows 24 in a direction generally normal to the first assembly face 18 and the second assembly face 22.

As shown in FIG. 1, the first component 12 includes an attachment feature 26. The second component 20 may likewise include an attachment feature 28. The attachment feature 26 of the first component 12 may cooperative with the attachment feature 28 of the second component 20 to secure the second component 20 to the first component 12.

Figure 2:
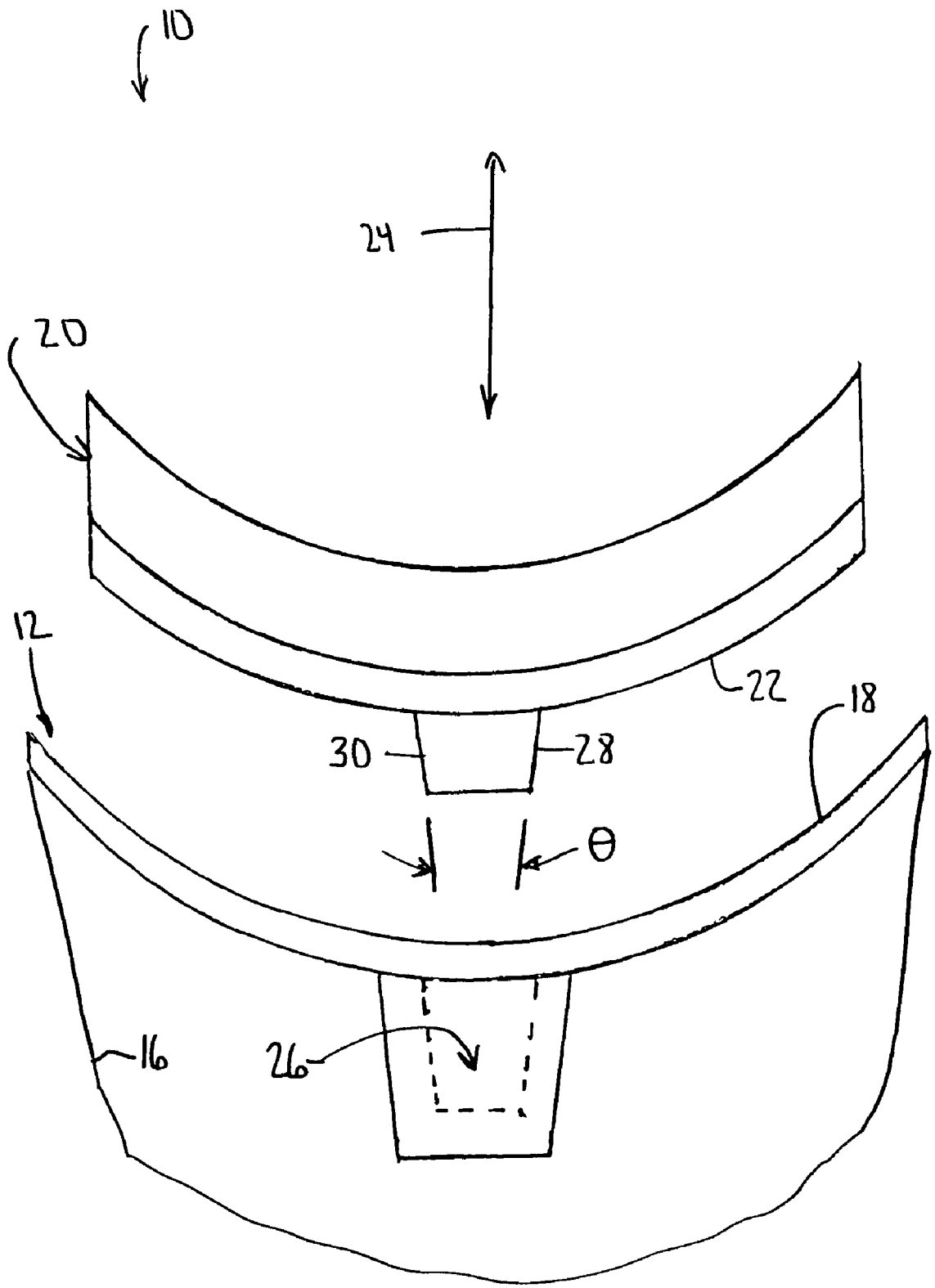
FIG. 2 is an exploded plan view of the metal backed plastic articulating modular glenoid assembly of FIG. 1.

Referring now to FIG. 2, the glenoid implant assembly 10 is shown disassembled. As shown in FIG. 2, the first component attachment feature 26 may be in the form of a female taper 26 and the second component attachment feature may be in the form of a male taper 28. The female taper 26 and the male taper 28 are preferably designed for intimate engagement therebetween. It should be appreciated that alternatively the first component attachment feature may be in the form of a male taper or have a generally conifrustical shape. Similarly, the second component attachment feature may be in the form of a female taper or have a cavity defining a generally conifrustical shape. Periphery 30 of the second component attachment feature 28 may define an included angle θ therebetween. The angle θ is selected to provide engagement between the first component attachment feature 26 and the second component attachment feature 28. The angle θ may be selected to provide for a secure or self-locking connection between the first component 12 and the second component 20. For a typical material and surface finish the angle θ may be, for example, from about 0° to 25°.

Figure 2A:
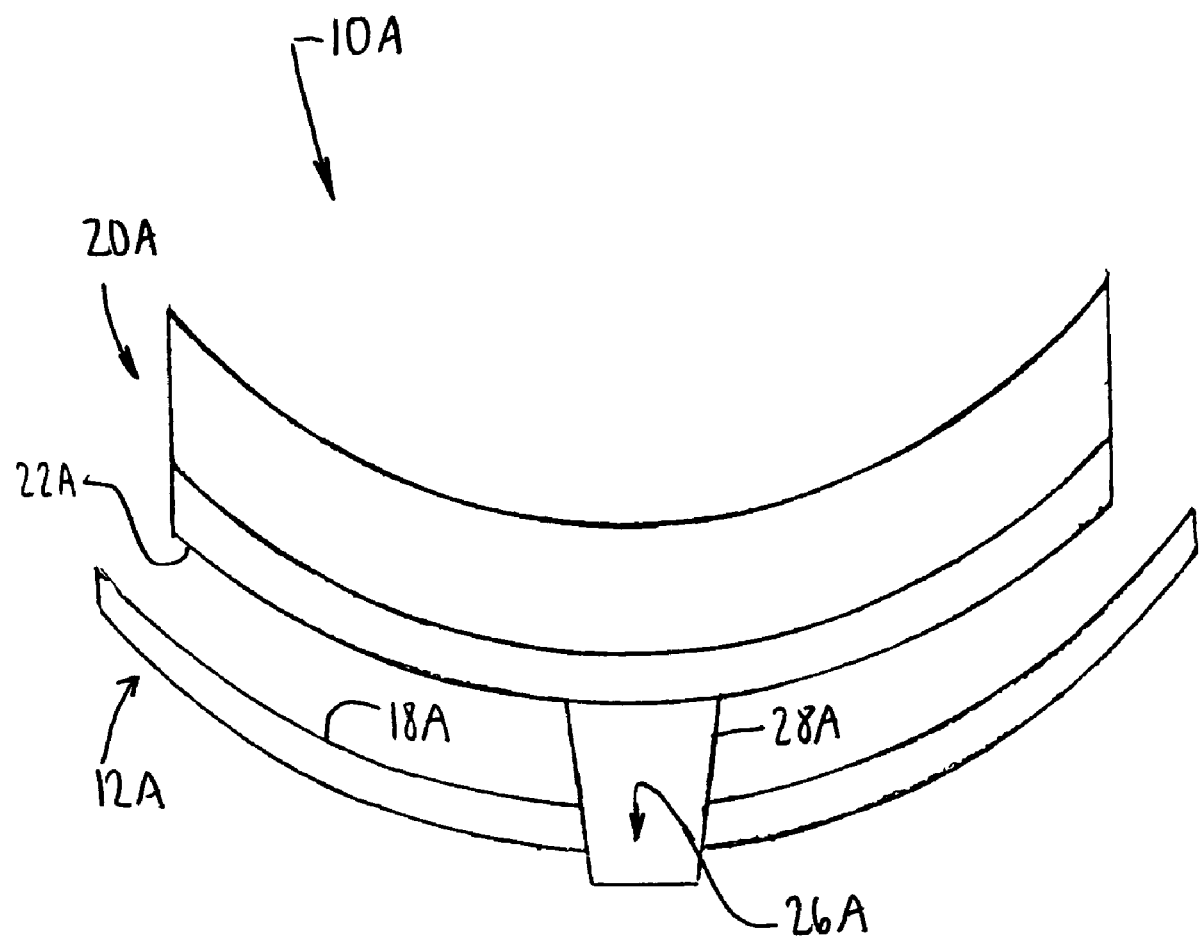
FIG. 2A is a plan view partially in cross-section of another embodiment of the present invention in the form of a modular glenoid assembly with spaced apart components.

To provide for a self-locking taper the angle θ may be determined by maintaining the formula:

$\tan(\theta/2) \geq m$ where:
θ=the included angle of the taper
m=coefficient of friction of the surface of taper Referring now to FIG. 2A an alternate embodiment of the glenoid implant assembly of the present invention is shown in glenoid assembly implant 10A. Glenoid implant assembly 10A is similar to the glenoid implant assembly 10 of FIG. 2 except that the glenoid implant assembly 10A configured such that the assembly face 18A of the first component 12A is spaced from or not in contact with the assembly face 22 of the second component 20A. The second component 20A is separated from by the first component 12A simply by the connection of the first component attachment feature 26A to the second component attachment feature 28A.

Figure 2B:
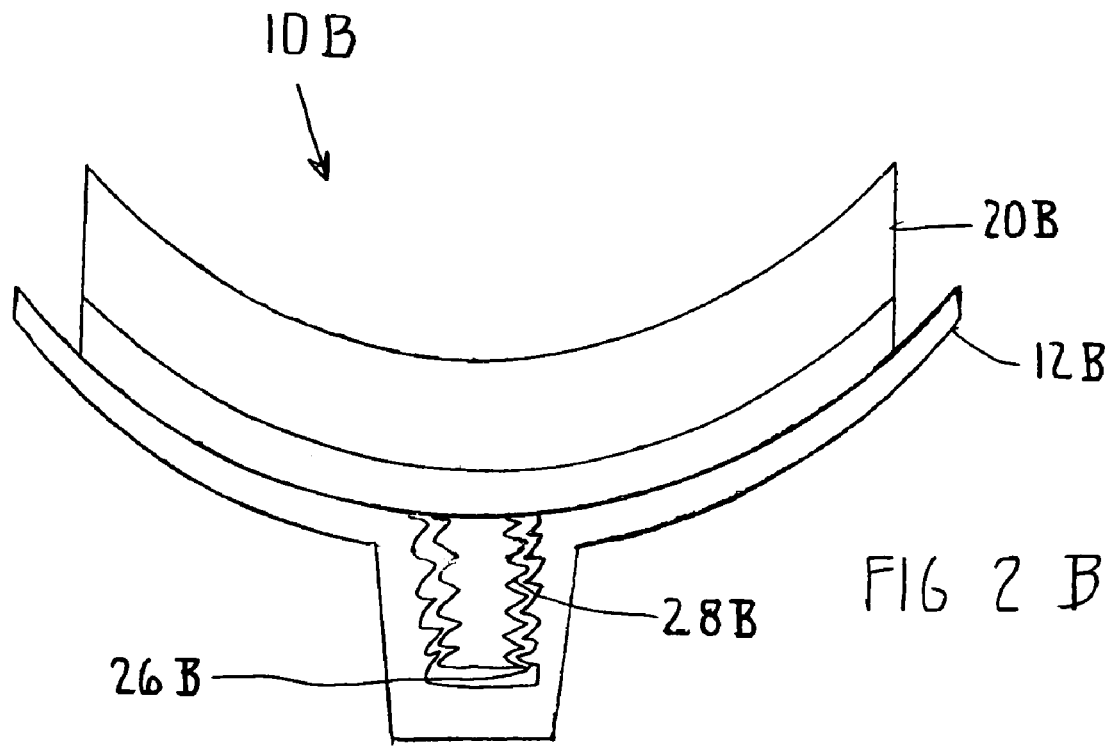
FIG. 2B is a plan view partially in cross-section of another embodiment of the present invention in the form of a modular glenoid assembly with a threaded connection.

Referring now to FIG. 2B an alternate embodiment of the present invention is shown as glenoid implant assembly 10B. Glenoid implant assembly 10B of FIG. 2B is similar to the glenoid implant assembly 10 of FIGS. 1 and 2 except that the glenoid implant assembly 10B of FIG. 2B includes a threaded connection of the first component 12B to the second component 20B of a threaded connection.

The glenoid implant assembly 10B is similar to the glenoid implant assembly 10 of FIGS. 1 and 2 and includes a first component 12B, which is secured to second component 20B. The glenoid implant assembly 10B has an attachment feature different than that of the glenoid implant assembly 10 of FIGS. 1 and 2.

For example and is shown in FIG. 2B the glenoid implant assembly 10B includes a first component attachment feature 26B in the form of a cavity defining internal threads which mates with a second component attachment feature 28B in the form of external threads. The external threads 28B of the second component 20B are threadably engagable with the internal threads 26B of the first component 12B.

Figure 2C:
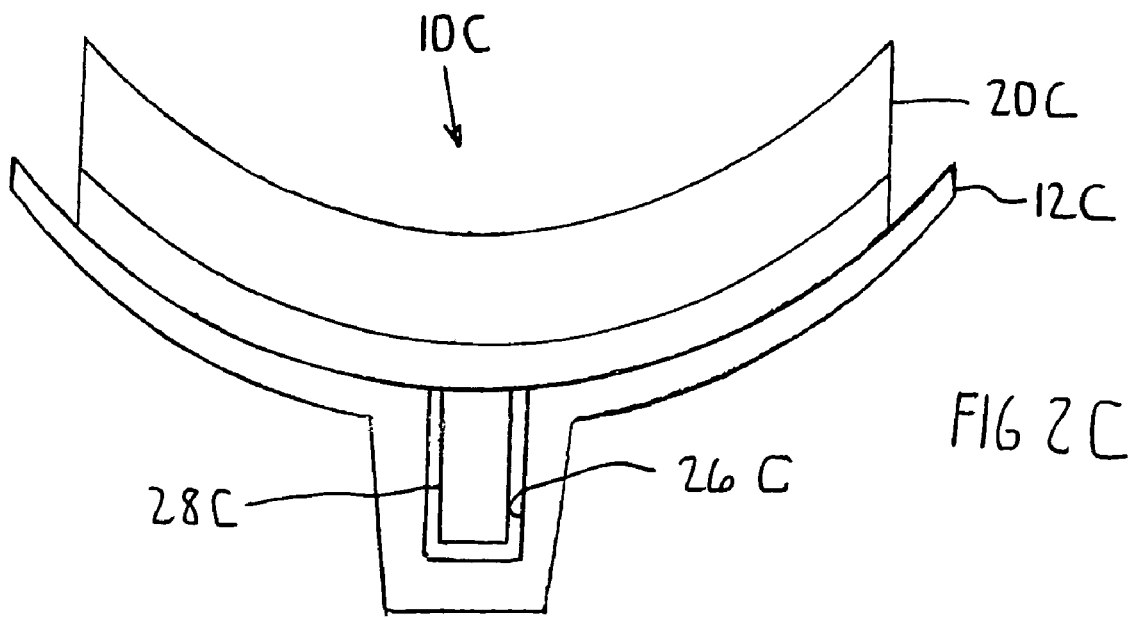
FIG. 2C is a plan view partially in cross-section of another embodiment of the present invention in the form of a modular glenoid assembly with a press-fit connection.

According to the present invention and referring now to FIG. 2C another embodiment of the present invention is shown as glenoid implant assembly 10C. Glenoid implant assembly 10C is similar to the glenoid implant 10 of FIGS. 1 and 2 and includes a first component 12C, which is matingly fitted to the second component 20C. The glenoid implant assembly 10C is different from the glenoid implant assembly 10 of FIGS. 1 and 2 in that the glenoid implant assembly 10C includes a first attachment feature 26C in the form of a generally cylindrical opening as well as a second attachment feature 28C extending from the second component 20C in the form of a cylindrical protrusion. The first component 12C is secured to the second component 20C by an interference fit between the cylindrical opening on cavity 26C and the cylindrical protrusion 28C.

Figure 2E:
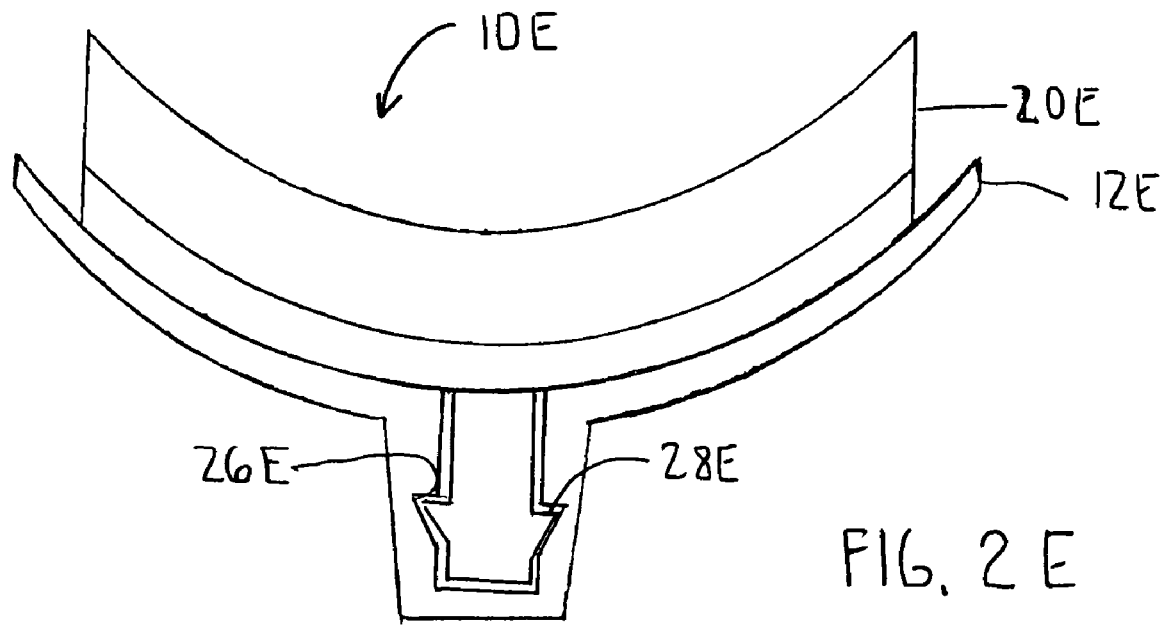
FIG. 2E is a plan view partially in cross-section of another embodiment of the present invention in the form of a modular glenoid assembly with a snap-fit connection.
Figure 2D:
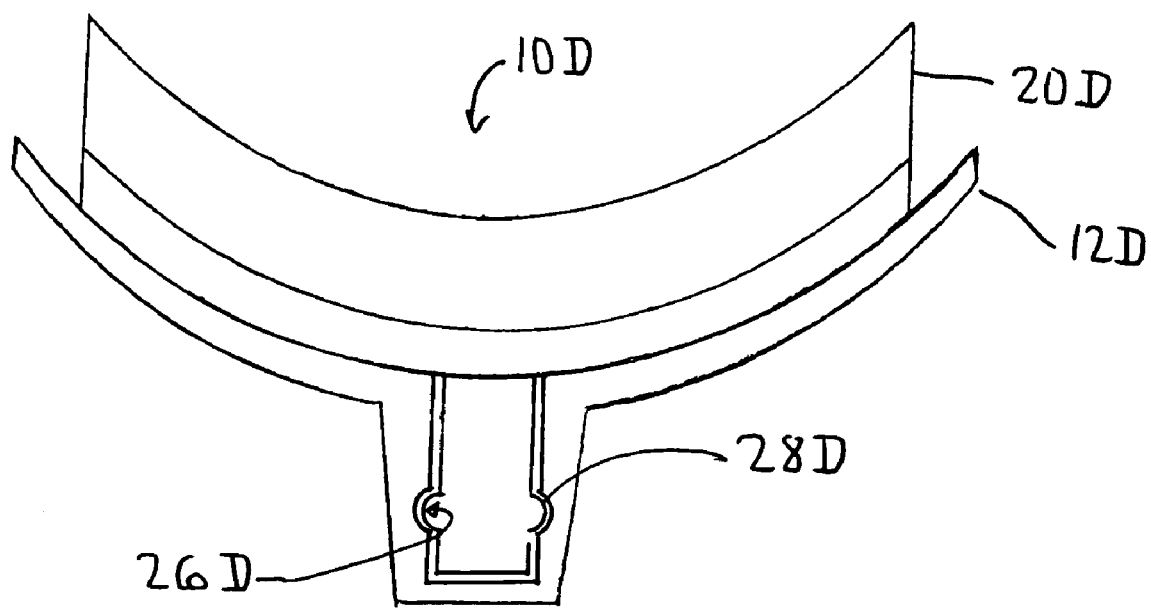
FIG. 2D is a plan view partially in cross-section of another embodiment of the present invention in the form of a modular glenoid assembly with a ribbed connection.

Referring now to FIG. 2D another embodiment of the present invention is shown as glenoid implant assembly 10D. The glenoid implant assembly 10D includes a first component 12D which is secureably fastened to the second component 20D. The glenoid implant assembly 10D is different from the glenoid implant assembly 10 of FIGS. 1 to 2 in that the glenoid implant assembly 10D includes a first component attachment feature 26D in the form of an internal groove formed into a cavity on the first component 12D which cooperates with an external rib 28D formed on a protrusion extending from second component 20D. The external rib 28D matingly fits into the internal groove 26D.

Yet another embodiment of the present invention is shown as glenoid implant assembly 10E. The glenoid implant assembly 10E is similar to the glenoid implant assembly 10 of FIGS. 1 and 2. For example, and is shown in FIG. 2E, the glenoid implant assembly 10E includes a first component 12E which is matingly secured to a second component 20E.

The glenoid implant assembly 10E is different from the glenoid implant assembly 10 of FIGS. 1 and 2 in that the glenoid implant assembly 10E includes a first component attachment feature 26E in the form of an internal notch formed in the first component 12E which matingly engages with an external lip 28E formed on a protrusion extending from second component 20E. The internal notch 26E mates with the external lip 28E to form a secure connection of the first component 12E to the second component 20E.

Figure 2F:
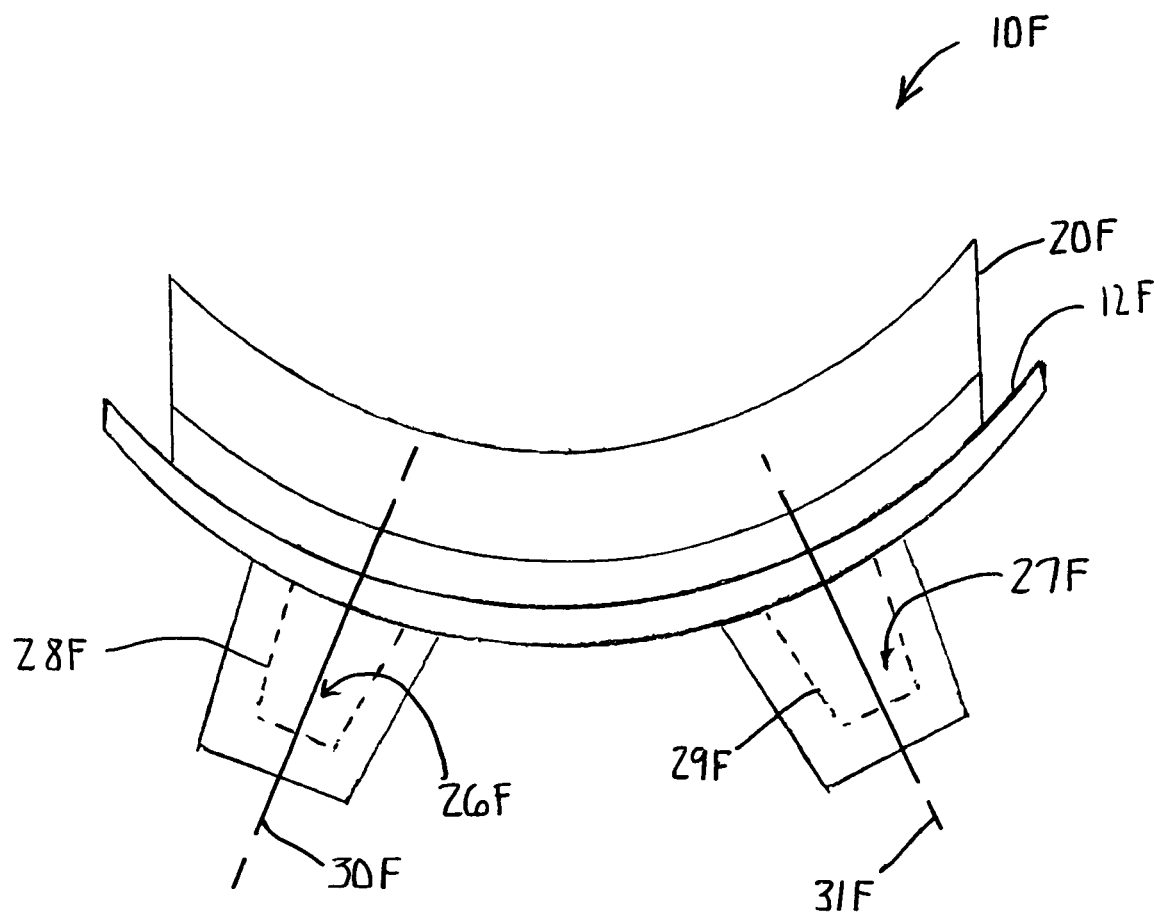
FIG. 2F is a plan view partially in cross-section of another embodiment of the present invention in the form of a modular glenoid assembly with 2 connections.
Figure 3:
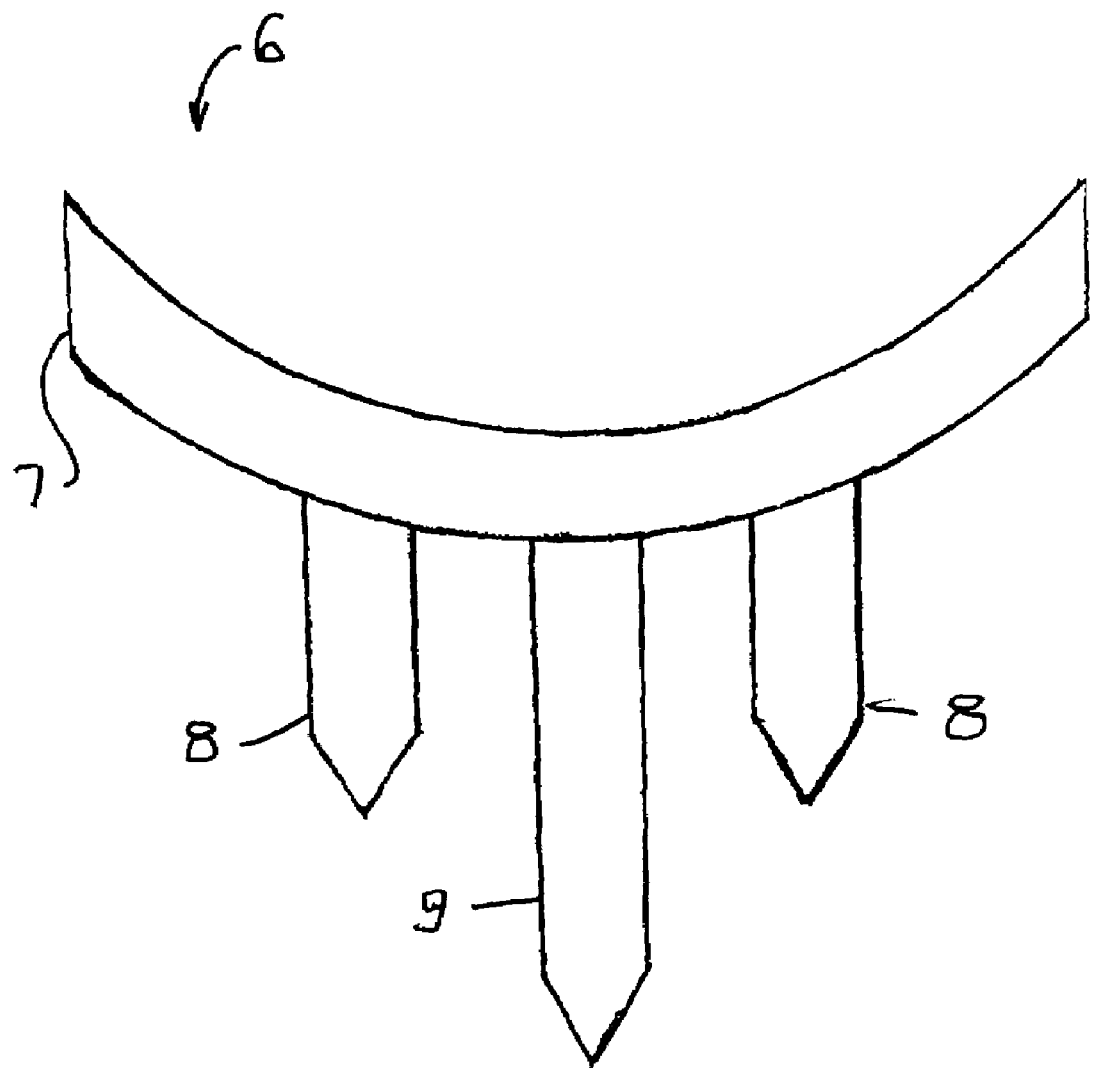
FIG. 3 is a plan view partially in cross-section of an all plastic prior art glenoid component.
Figure 4:
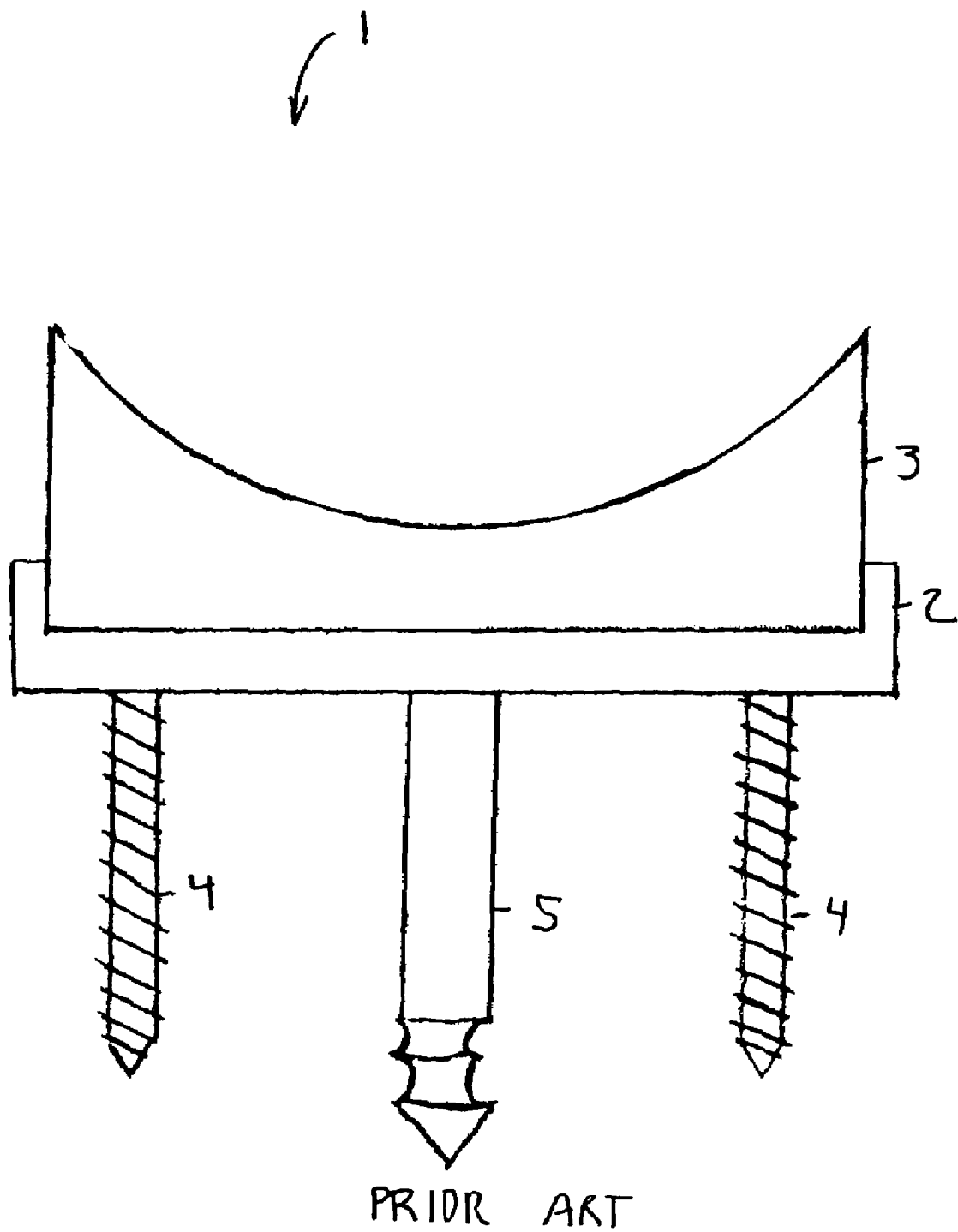
FIG. 4 is a plan view partially in cross-section of a metal backed prior art glenoid component.

Referring now to FIG. 2F another embodiment of the present invention is shown as glenoid implant assembly 10F. The glenoid implant assembly 10F is similar to the glenoid implant assembly 10 of FIGS. 1 and 2 and includes a first component 12F which is matingly secured to a second component 20F. The glenoid implant assembly 10F of FIG. 2F is different from the glenoid implant assembly 10 of FIGS. 1 and 2 in that the glenoid implant assembly 10F has a pair or two separate attachment features.

For example and is shown in FIG. 2F the glenoid implant assembly 10F includes a first external protrusion 28F as well as a second spaced apart external protrusion 29F. Both protrusion 28F and 29F extend from the second component 20F. The first external protrusion 28F mates with first internal cavity 26F formed in the first component 12F. Similarly, a second internal cavity 27F is formed on the first component 12F and mates with second external protrusion 29F. Centerlines 30F of 31F of protrusion 28F and 29F respectively may be parallel to each other and may be normal to or at acruate angle to the first component 12F. The acruate angle may assist in minimally invasive procedures.

Figure 5:
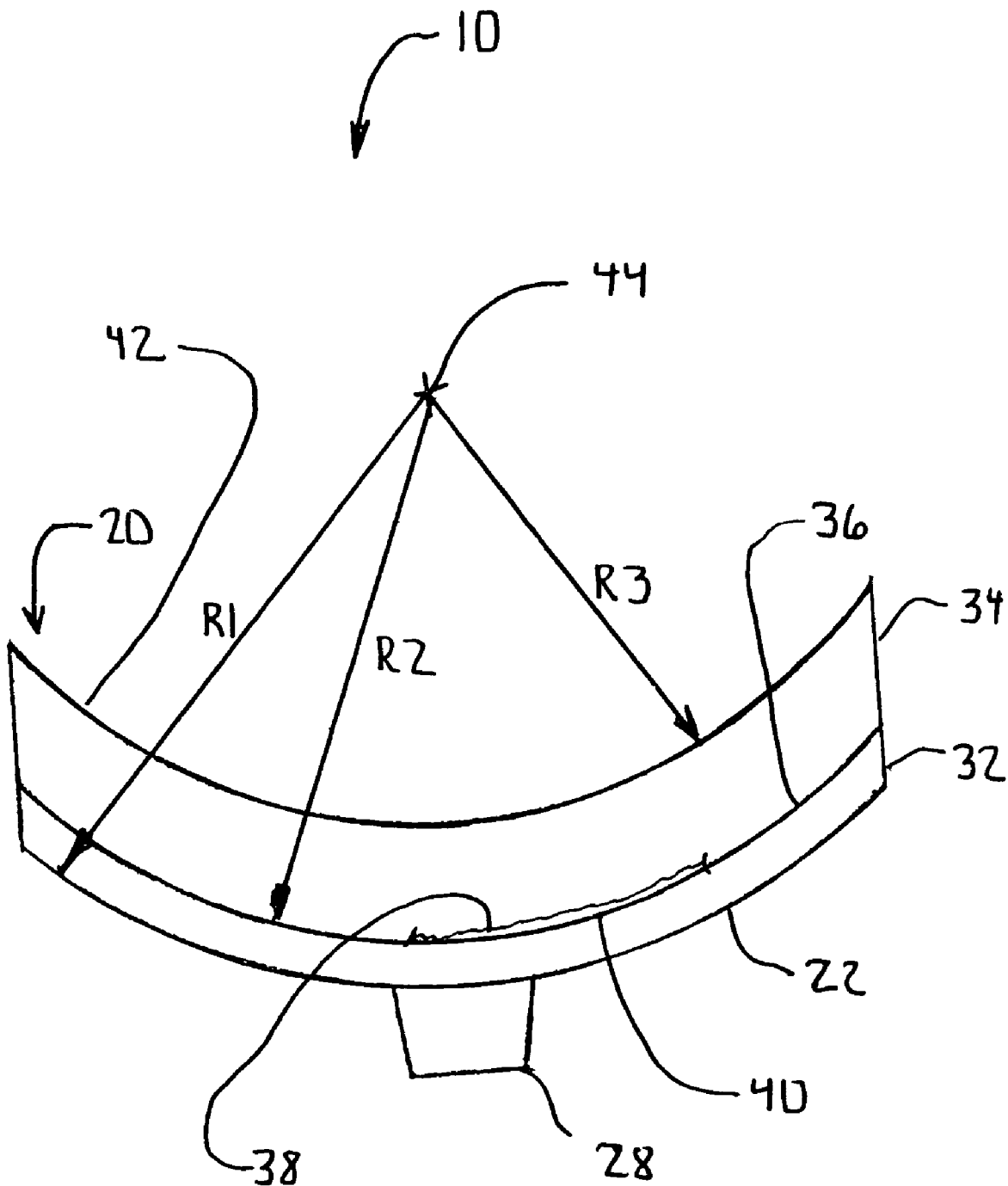
FIG. 5 is a plan view partially in cross-section of the metal backed plastic articulating component of FIGS. 1 and 2.

Referring now to FIG. 5 the second component 20 of the modular glenoid assembly 10 is shown in greater detail. This second component 20 may be made of any suitable durable material and may for example be made of a metal, a composite, a ceramic or a plastic. The second component 20 is preferably made from a material that may be sterilized by a currently available sterilizing technique such as gas plasma, gamma irradiation, ETO, or by autoclaving.

The second component 20 may be of a one piece or unitary design or may, as shown in FIG. 5, be modular or made of more than one component. If made of more than one component, the second component 20 may include a first portion 32 which may include the external taper connection 28 and a second portion 34 connected to the first portion 32. Since, as is shown in FIG. 5, the first portion 32 includes the tapered connection 28, the first component 32 is preferably made of a rigid material to obtain a secure tapered connection to the first component 12. For example and is shown in FIG. 5, the first portion 32 may be in the form of a metal backing.

The first portion 32 may be made of any suitable durable material for example a metal. If made of a metal the metal backing 32 may be made for example a cobalt chromium alloy, a stainless steel alloy, or a titanium alloy. Metal backing 32 includes the assembly face 22 as well as a connecting face 36 opposed to the assembly face 22.

The connecting face 36 may include a feature 38 on the connecting face 36 for enhancing the securing of the second portion 34 of the second component 20 to the first portion 32 of the second component 20. The feature 38 may, for example, be in the form of a roughened surface or may include a coating, for example, a porous coating. For example, the feature 38 may be in the form of a Porocoat® surface as provided by DePuy Orthopaedics Warsaw, Ind. The Porocoat® coating is more fully described in U.S. Pat. No. 3,855,638 to Pilliar hereby incorporated by reference in its entirety.

The second portion 34 of the second component 20 may, as shown in FIG. 5, be in the form of a plastic bearing. The plastic bearing 34 may include a connecting face 40 for contact with the first portion 32. The contacting face 40 cooperates with contacting face 36 of the first portion 32. The plastic bearing 34 may also include a concave articulating surface 42 for cooperation with the humeral component of a total shoulder joint. The plastic bearing 34 may be made of any suitable, durable material and may, as shown in FIG. 5, be made of an ultra-high molecular weight polyethylene. For example, the ultra-high molecular weight polyethylene may be a cross-linked, ultra-high molecular weight polyethylene. For example the plastic bearing 34 may be made of a material in the form of a Marathon® plastic as described in U.S. Pat. No. 6,281,264 to McKellop.

The second component 20 of the modular glenoid assembly 10 may have any suitable shape to form a glenoid for cooperation with a humeral component to form a total shoulder. For example, the second component 20, as shown in FIG. 5, may include the first portion 32 with the assembly face 22 of the second component 20 in having a generally convex surface defined by a portion of a sphere. For example, as shown in FIG. 5, the assembly face 22 may be defined by a radius R1 extending from origin 44. Similarly the first portion 32 of the second component 20 may further be defined by the connecting face 36 having a generally concave surface. The concave connecting face 36 may be in the form of a portion of a sphere and be defined by a radius R2 extending from the origin 44.

Similarly, the concave articulating surface 42 of the second portion 34 of the second component 20 may have a concave shape as shown in FIG. 5 and may be defined by a portion of a sphere. The concave articulating surface 42 may be, for example, and as is shown in FIG. 5 be defined by a radius R3 extending from origin 44.

It should be appreciated that the second portion 34 of the second component 20 of the modular glenoid assembly 10 which forms the articulating surface of the glenoid assembly 10 may be made of any suitable material that is proven to work as an articulating surface for an artificial joint. For example the second portion 34 may be made of a plastic, a metal, a composite, or a ceramic. In fact, a feature of the invention is that the second component 20 may be removed from the first component 12 in such a way that the first component 12 may remain secured to the glenoid fossa in order that a alternate or a replacement articulating surface may be placed in the patient while the first component 12 remains secured to this glenoid fossa.

Figure 7:
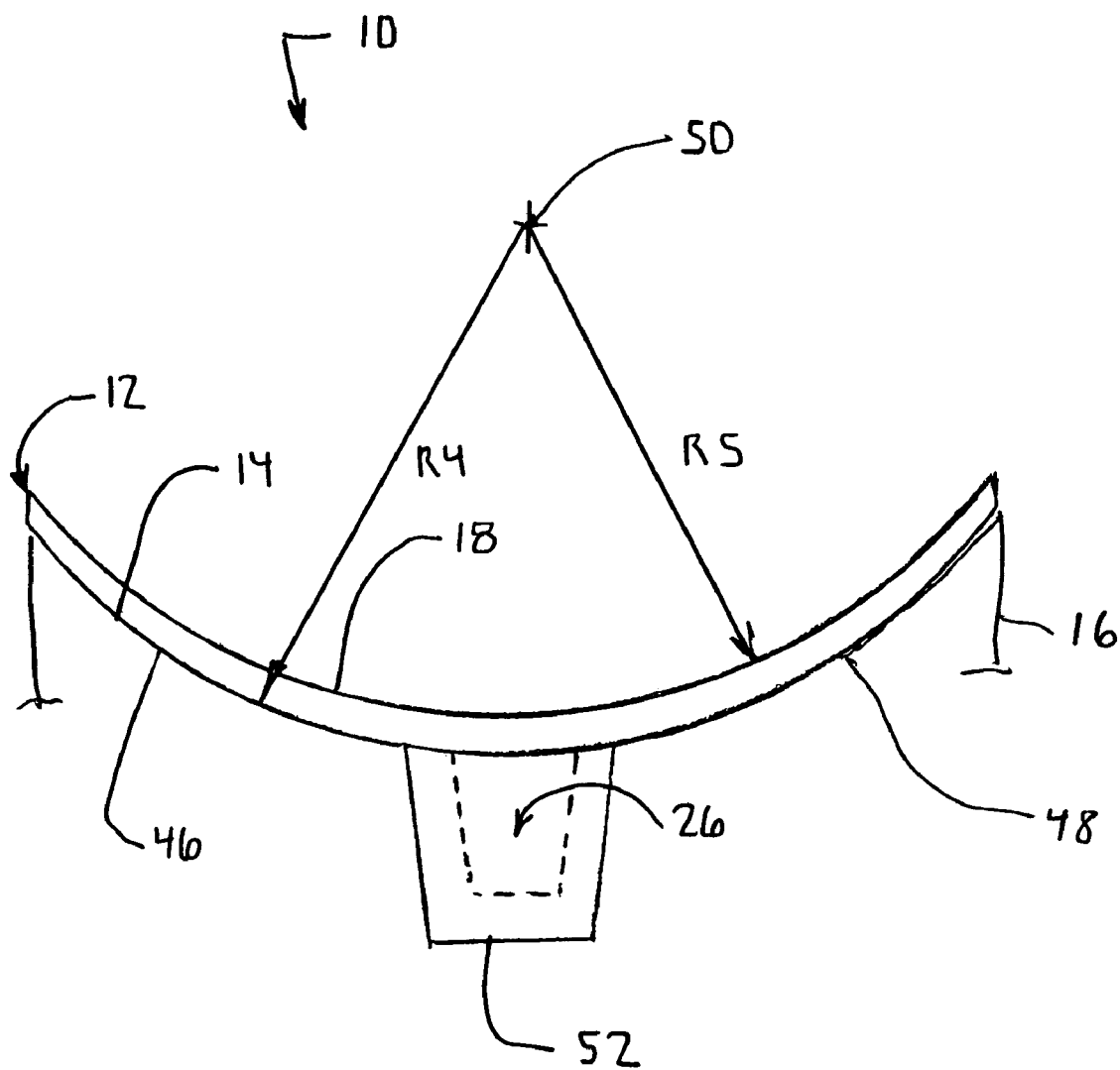
FIG. 7 is a plan view partially in cross-section of the fixation component of the modular glenoid assembly 1 and 2.

Referring now to FIG. 7 the first component 12 of the modular glenoid assembly 10 is shown in greater detail. The first component 12 of the modular glenoid assembly 10 may, as shown in FIG. 7, be unitary or of a one-piece construction. Alternatively, it should be appreciated, that the second component 12 may be made of a multiple components or may be modular.

The first component 12 may be made of a suitable, durable material capable for providing support. For the second component 20 for example and is shown in FIG. 7, the first component 12 is made of a metal. If made of a metal, the first component 12 may be made of, for example, cobalt chromium alloy, a stainless steel alloy, or a titanium alloy. It should be appreciated that the first component 12 may be made of a ceramic, a composite, or a plastic. The first component 12 as shown in FIG. 7 includes a glenoid surface 46 which is opposed to the assembly face 18 of the first component 12. The glenoid surface 46 fits against the glenoid fossa 14 of the scapula 16.

The glenoid surface 46 may, as is shown in FIG. 7, include a fixation feature 48 located on the glenoid surface 46. The fixation feature 48 may be in the form for example a roughened surface or an exterior coating. For example the fixation feature 48 may be in the form of a coating applied to the surface 46 and may for example be a porous coating. If a porous coating the fixation feature 48 may be for example a Porocoat® porous coating.

The first component 12 of the modular glenoid assembly 10 may have any suitable shape and may as shown in FIG. 17 include the glenoid surface 46 having a generally convex surface. For example the glenoid surface 46 may be in the form of a portion of a sphere and may be defined by a radius R4 extending from origin 50. Similarly, the first component 12 may include the assembly face 18 having a generally concave shape. The assembly face 18, as shown in FIG. 7, may be in the form of a portion of a sphere and may be defined by radius R5 extending from origin 50.

In order for the first component 12 to include the attachment feature 26 in the form of an internal taper the first component 12 may include a protrusion 52 extending outwardly from the glenoid surface 46. The protrusion 52 may have a shape generally similar to the internal taper attachment feature 26. It should be appreciated that the protrusion 52 may have any shape capable of accommodating the attachment feature 26 and that the protrusion 52 may assist in providing anchoring of the first component 12 into the glenoid.

Figure 6:
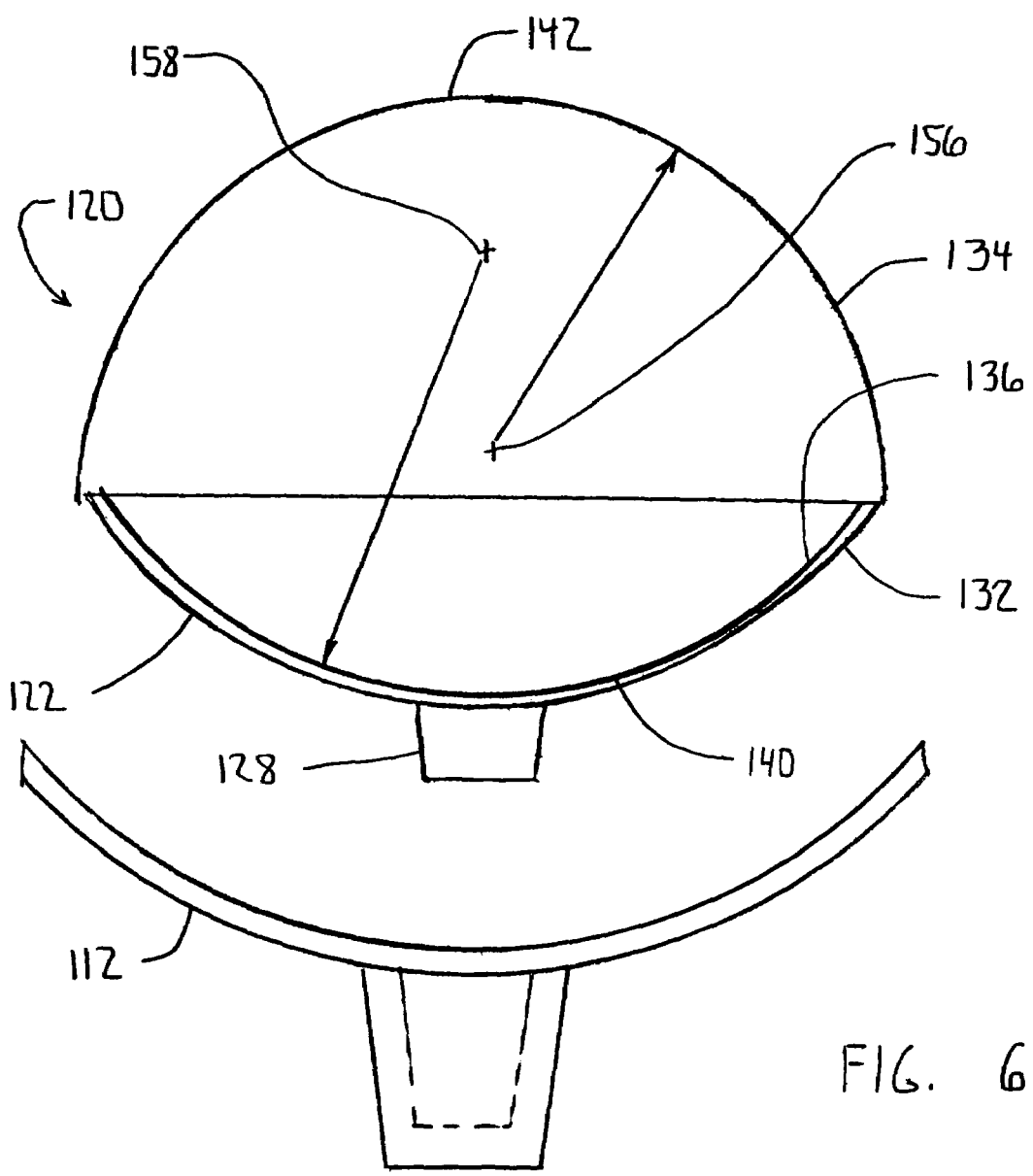
FIG. 6 is a plan view partially in cross-section of a metal backed plastic articulating component of a modular glenoid assembly with a tapered connection and a convex articulating surface according to another embodiment of the present invention.

According to the present invention and referring to FIG. 6, another embodiment of the present invention is shown as modular glenoid assembly 100. The modular glenoid assembly 100 includes a first component 112 which may be similar or even identical to the first component 12 of the modular glenoid assembly 10 of FIGS. 1 and 2. The modular glenoid assembly 100 includes a second component 120, which is different than the second component 20 of FIG. 5.

For example and is shown in FIG. 6 the second component 120 includes a first portion 132 in the form of for example a metal backing. The metal backing 132 is similar to the metal backing or first portion 32 of the second component 20 of FIG. 5. The metal backing 132 includes the assembly face 122 as well as the opposed connecting face 136. The metal backing 132 also includes the external tapered portion 128, which extends from the assembly face 122.

The second component 122 also includes a second portion 134. The second portion 134 like the second portion 34 of the second component 20 of FIG. 5 is made of a material suitable for prosthetic articulation. For example, the second portion 134 may be made of, for example, a metal, a plastic, or a ceramic. For example, the second portion 134 may be made of a plastic for example ultra-high molecular weight polyethylene, for example, a cross-linked, ultra-high molecular weight polyethylene. The second portion 134 includes a connecting face 140 which mates with connecting face 136 of the first portion 132. The second portion 134 also defines a convex articulating surface 142.

The convex articulating surface 142 may be generally convex and may, for example, be in the form of a portion of a sphere. For example the articulating surface 142 may be defined by a radius R6 extending from origin 156. Generally the connecting face 140 may be generally convex and may be in the form of a portion of a sphere. For example the connecting face 140 may be defined by a radius R7 extending from origin 158.

Figure 8:
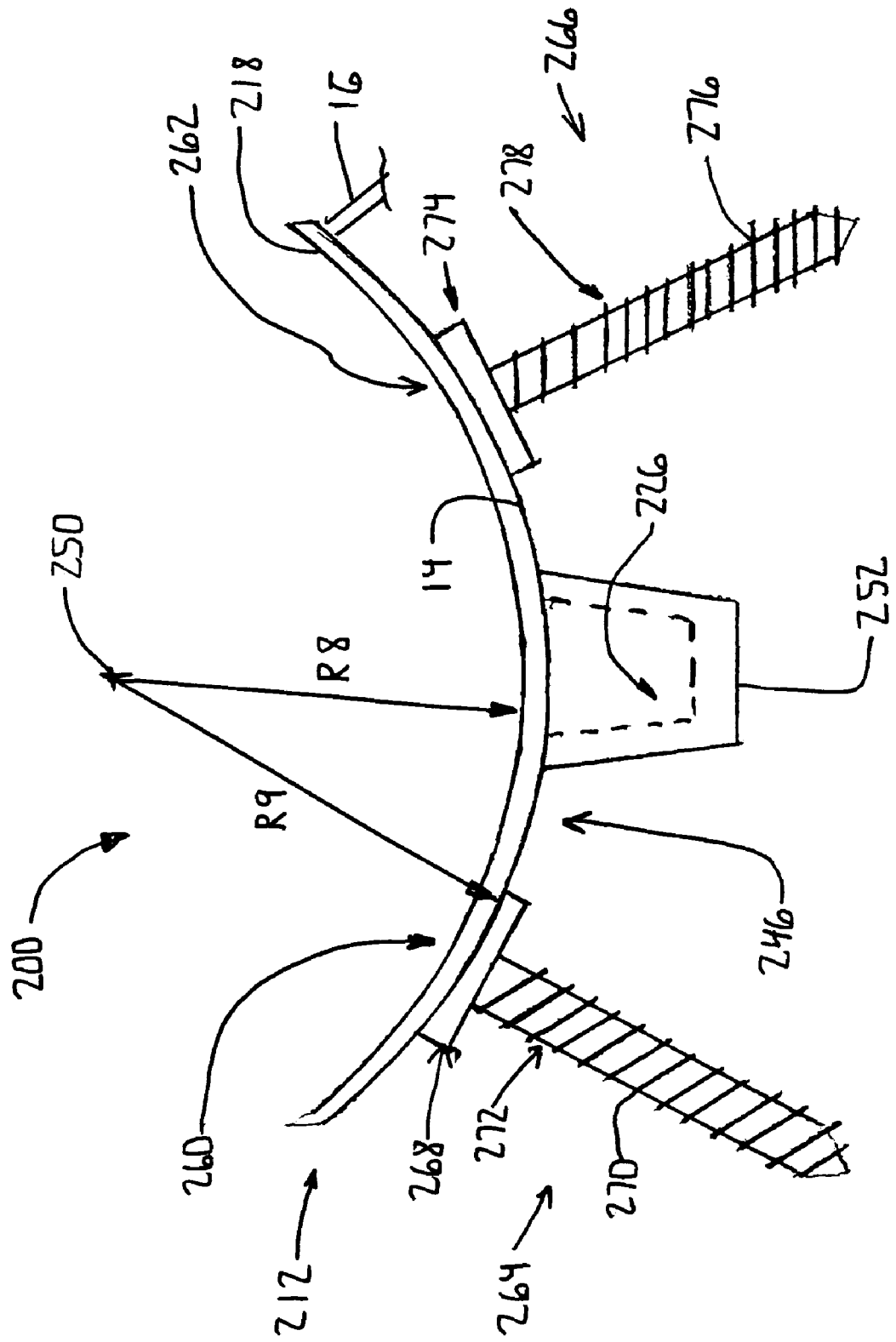
FIG. 8 is a plan view partially in cross-section of a fixation component of a modular glenoid assembly with a tapered connection and with screw fixation for use with the articulation component of FIG. 6 according to another embodiment of the present invention.

Referring now to FIG. 8, another embodiment of the present invention is shown as modular glenoid assembly 200. The modular glenoid assembly 200 includes a second component or articulation component (not shown) which may be similar or identical to the second component 20 of FIG. 5. The modular glenoid assembly 200 further includes a first component or fixation component 212 as shown in FIG. 8. The fixation component 212 is generally similar to the first component 12 of FIG. 7 and includes a concave assembly face 218.

The assembly face 218 may be in the form of a portion of a sphere and may be defined by a radius R8 extending from origin 250. Similarly, the fixation component 212 may include a glenoid surface 246 which may be convex. The glenoid surface 246 may, as shown in FIG. 8, be in the form of a portion of a sphere and be defined by a radius R9 extending from origin 250. The fixation component 212 may include a female taper 226 formed in protrusion 252 extending from the glenoid surface 246 of the fixation component 212.

Unlike the first component 12 of FIG. 7, the fixation component 212 of FIG. 8 includes a first opening 260 and a spaced apart second opening 262. The openings 260 and 262 extend through the fixation component 212 from the assembly face 218 through the glenoid surface 246. The openings 260 and 262 are adapted to receive fasteners for assisting in the securement of the fixation component 212 to the glenoid fossa 14 of the scapula 16.

For example as shown in FIG. 8 the modular glenoid assembly 200 further includes a first screw 264 which matingly fits with the first opening 260 of the first component 212. The modular glenoid assembly 200 also includes a second screw 266 which mates with second opening 262 in the first component 212. First screw 264 includes a first screw head 268 for securing the screw 264 to the fixation component 212. The first screw 264 further includes first screw threads 270 formed on first screw shank 272. Generally the second screw 262 includes a second screw head 274 for securement to the fixation component 212. The second screw 266 also includes second screw threads 276 formed on second screw shank 278.

Figure 9:
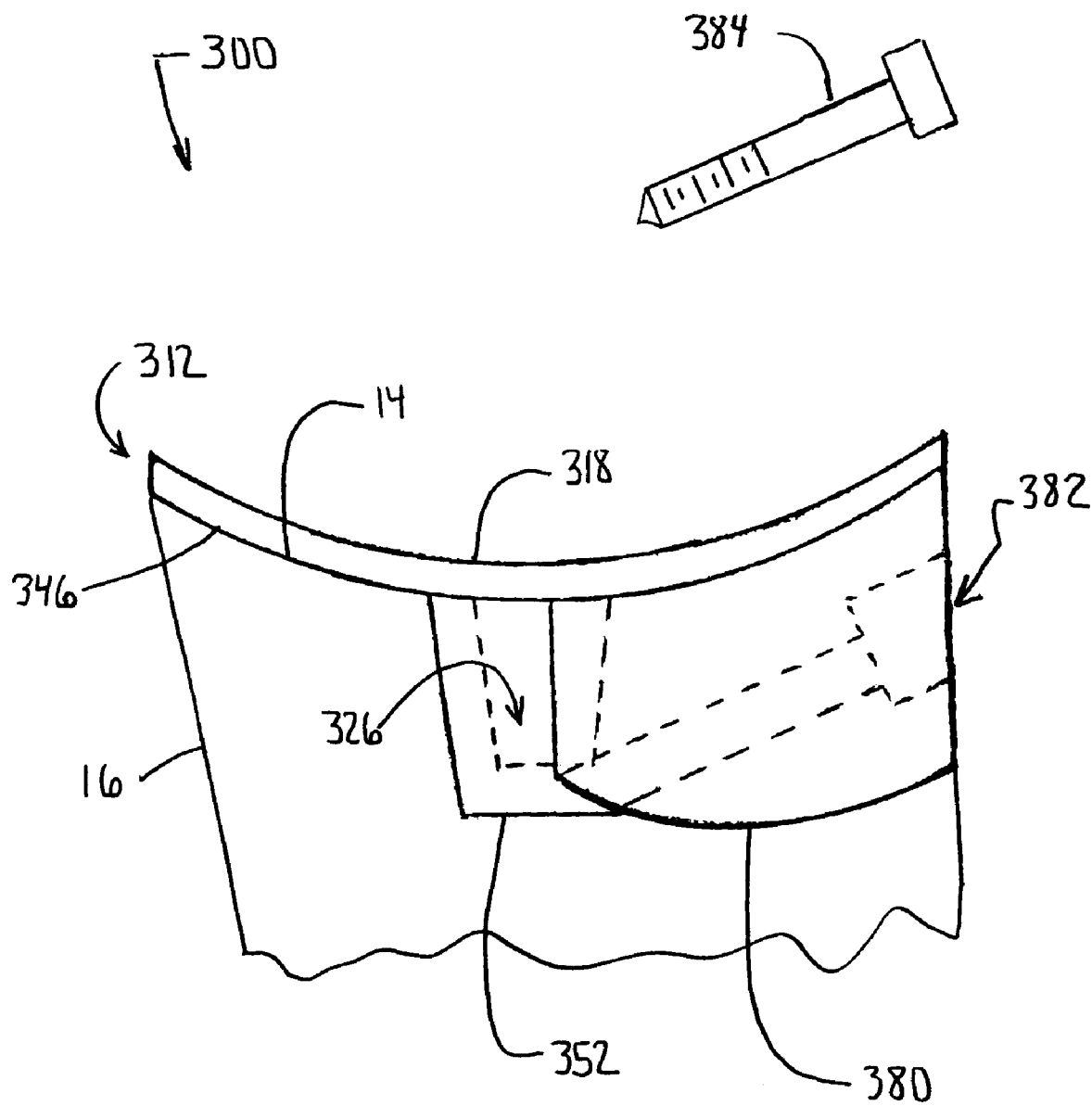
FIG. 9 is a plan view partially in cross-section of a fixation component of a modular glenoid assembly with a tapered connection and with a posterior augmentation portion for use with the articulation component of FIG. 6 according to another embodiment of the present invention.

According to the present invention and referring to FIG. 9 another embodiment of the present invention is shown as modular glenoid assembly 300. The modular glenoid assembly 300 includes an articulating component (not shown) similar to or identical to the articulating component or second component 20 of FIG. 5. The modular glenoid assembly 300 also includes the first fixation component 312.

The first component 312 is somewhat similar to the first component 12 the modular glenoid assembly 10 of FIG. 7 and includes a glenoid surface 346 for placement against the glenoid fossa 14 of the scapula 16 as well as an opposed assembly face 318 opposed to the glenoid surface 346. The first component 312 further includes a protrusion 352 extending from the glenoid surface 346. An internal taper 326 is formed in a cavity formed in the protrusion 352.

Unlike the modular glenoid assembly 10 of FIG. 7, the modular glenoid assembly 300 of FIG. 9 further includes a augmentation 380. The augmentation 380 may be an anterior augmentation or as shown in FIG. 7 be in the form of a posterior augmentation. Posterior augmentation 380 may have any suitable shape and is provided to fill or replace a void caused by abnormal wear of the glenoid fossa 14. For example and as is shown in FIG. 9, the augmentation 380 is in the form of a protrusion extending downwardly from the glenoid surface 346. The augmentation 380 defines an opening 382 through the augmentation 380. The opening 382 is adapted for receiving a augmentation screw 384 for assisting in securing the fixation component 312 to the scapula 16. The augmentation screw 384 may be any suitable bone screw for example a cancellous screw or a cortical screw.

Figure 9A:
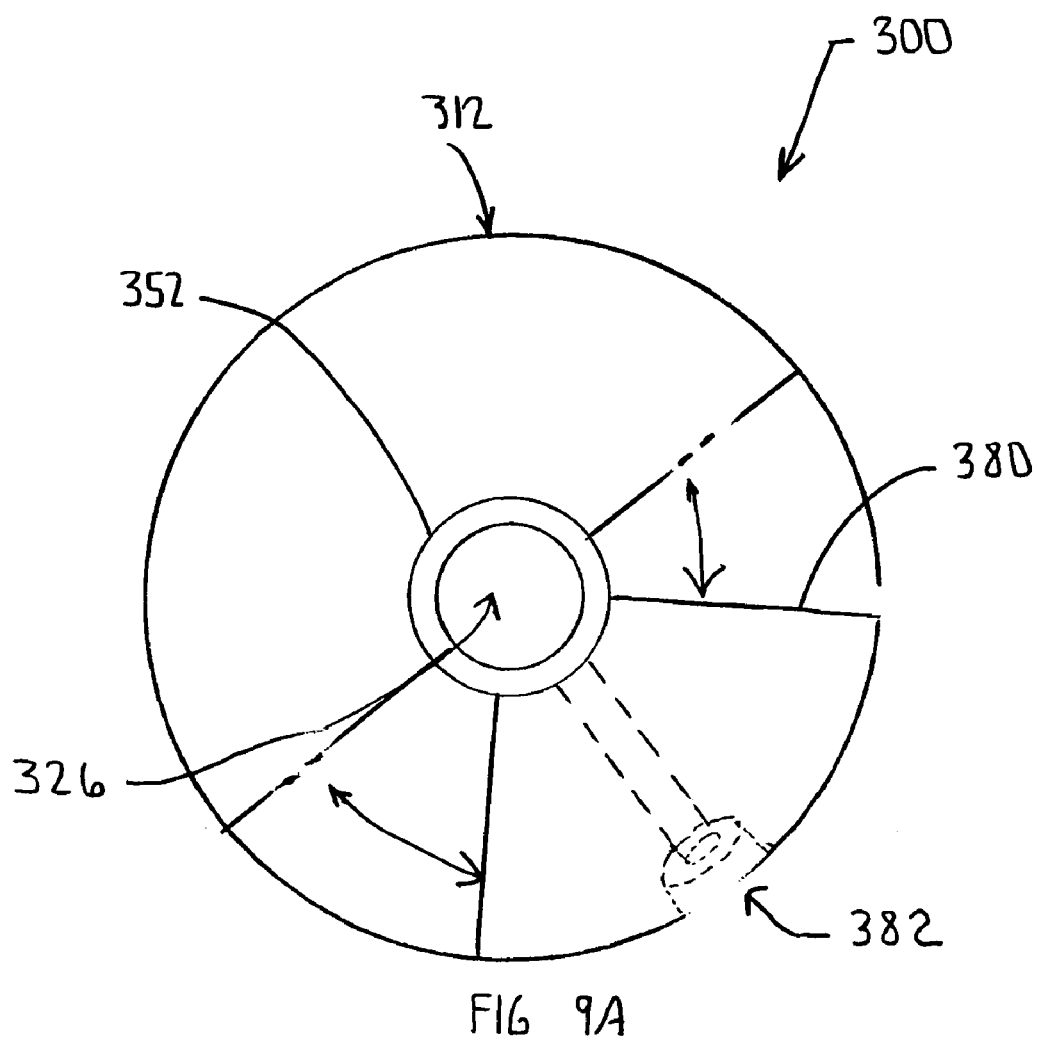
FIG. 9A is a bottom view of FIG. 9.

Referring now to FIG. 9A, the fixation component 312 of the modular glenoid assembly 300 is shown in greater detail. The fixation component 312 includes the posterior augmentation 380 assisting in providing support to a posteriorly eroded glenoid. The augmentation 380 may extend for 90° or for 180° as shown in phantom or any angle inbetween.

Figure 9B:
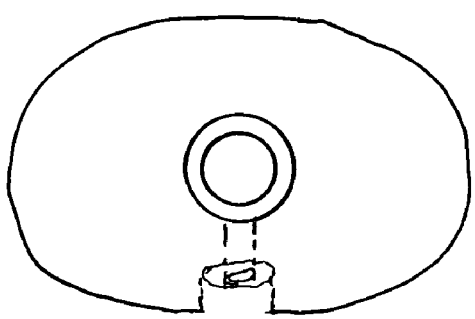
FIG. 9B is a bottom view of an elliptical modular glenoid assembly according to another embodiment of the present invention.

Referring now to FIG. 9B an elliptical modular glenoid assembly 300B is shown. The assembly 300B is similar to the assembly 300A of FIG. 9A except it is elliptical.

Figure 10:
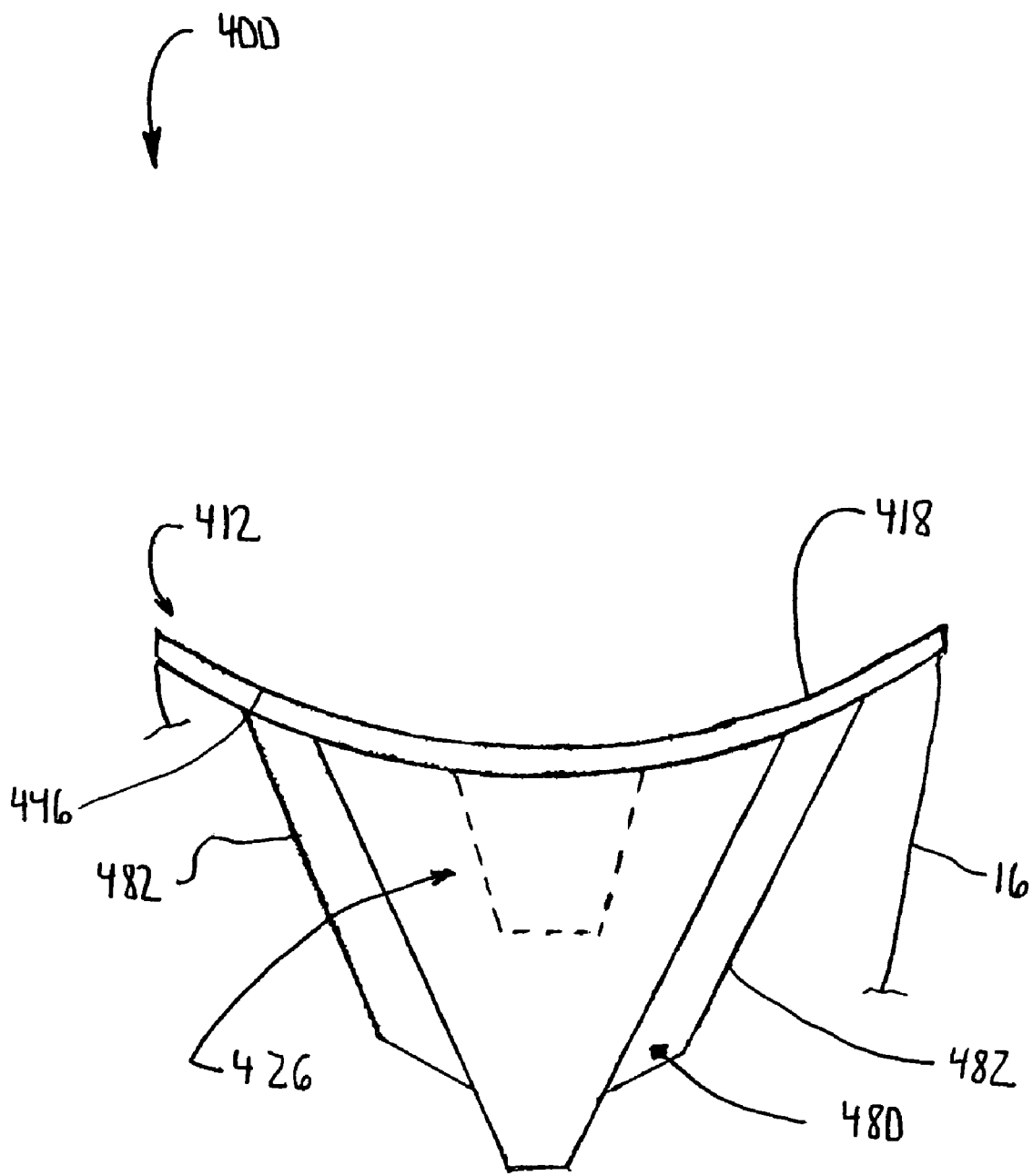
FIG. 10 is a plan view partially in cross-section of a fixation component of a modular glenoid assembly with a tapered connection and with a vault fixation portion and anti-rotation fins for use with the articulation component of FIG. 6 according to another embodiment of the present invention.

Referring now to FIG. 10 another embodiment of the present invention is shown as modular glenoid assembly 400. The modular glenoid assembly 400 is similar to the modular glenoid assembly 10 of FIGS. 1 and 2 and includes an articulation component (not shown) similar to or identical to articulation component 20 of the modular glenoid assembly 10 of FIG. 5. The modular glenoid assembly 400 further includes a fixation component 412 which is somewhat similar to the fixation component 12 of FIG. 7. The first component 212 includes an assembly face 418 as well as an opposed glenoid surface 446. The fixation component 412 further includes an attachment feature 426.

Figure 10A:
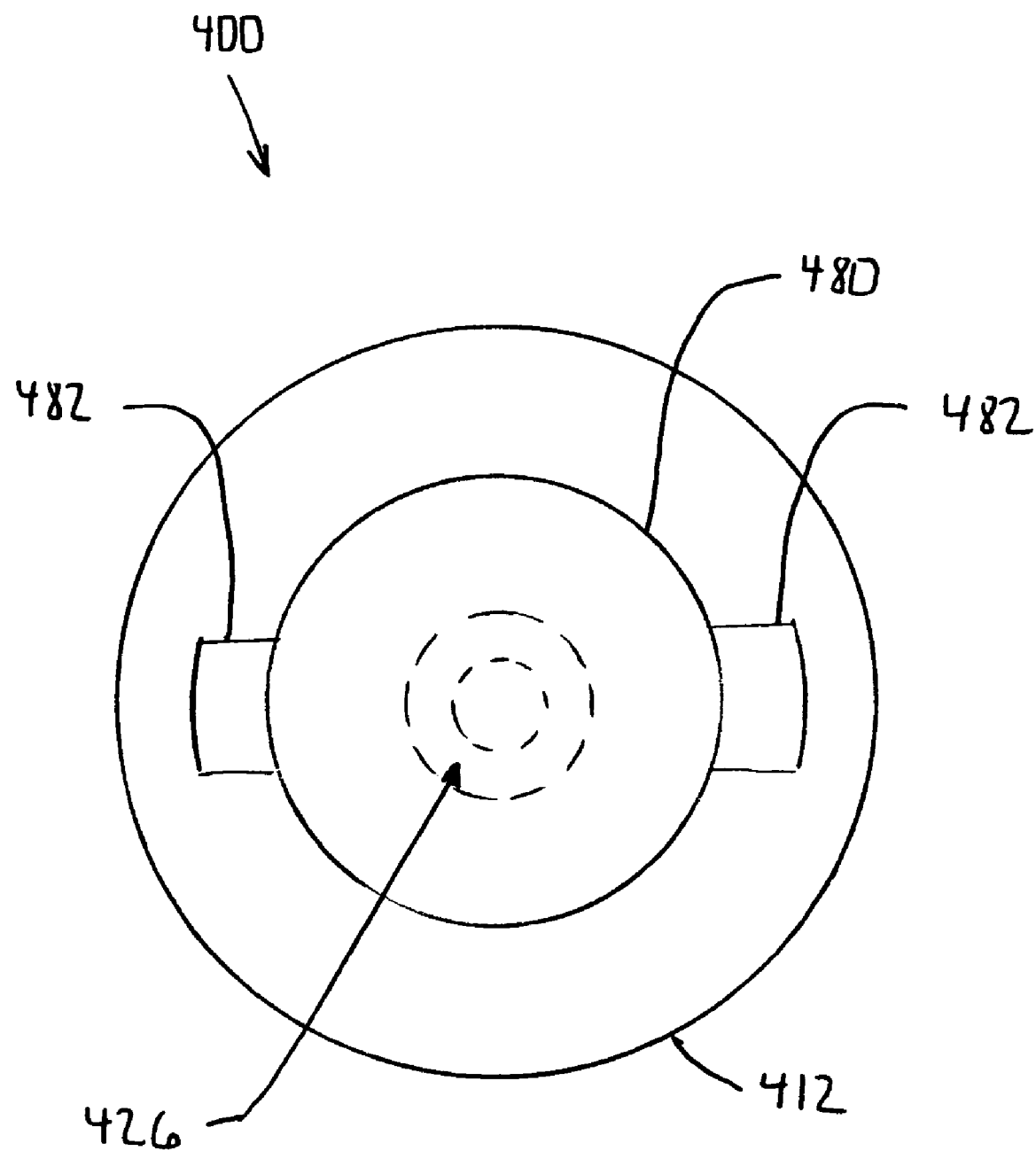
FIG. 10A is a bottom view of FIG. 10.

Referring now to FIGS. 10 and 10A, the modular glenoid assembly 400 is different from the modular glenoid assembly 10 of FIGS. 1, 2, 5 and 7 in that the modular glenoid assembly 400 further includes a vault fixation portion 480. The vault fixation portion 480 is used to provide for vault of internal scapula fixation for the modular glenoid assembly 400. The vault fixation portion 480 extends downwardly from the glenoid surface 446 of the fixation component 412. The vault fixation portion 480 may have any suitable shape and, as is shown in FIG. 10, may have a generally conifrustical shape. The vault fixation portion 480 may include a pair of spaced of apart anti-rotation fins 482. The anti-rotation fins 482 serve to securely position the fixation component 412 in the scapula 16. Vault fixation glenoid components are more fully described in U.S. patent application Ser. No. 10/259,045 entitled "Concave Resurfacing Prosthesis" incorporated herein by reference in its entirety.

Figure 11:
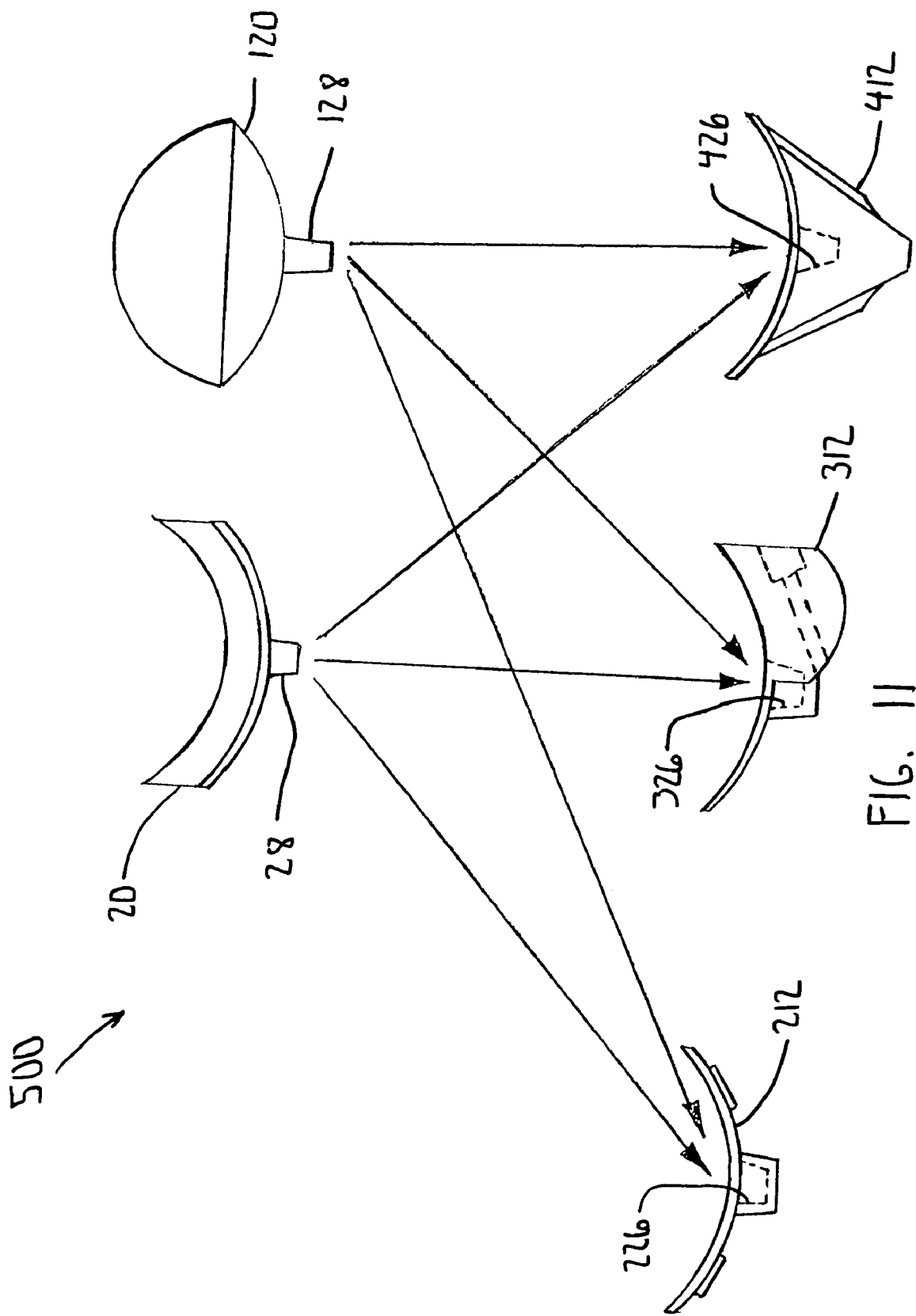
FIG. 11 is a plan view of a series of components that may form a kit with the components partially in cross-section including three fixation components of a modular glenoid assembly with a tapered connection, with an augmentation and with a vault fixation portion and two articulation components of a modular glenoid assembly with a convex articulation surface and with a concave articulation surface according to another embodiment of the present invention.

Referring now to FIG. 11, another embodiment of the present invention is shown as kit 500. The kit 500 includes a plurality of articulation components as well as a plurality of fixation components. As shown in FIG. 11 the kit 500 includes a first articulation component, for example, articulation component 20. The articulation component 20 is shown in greater detail in FIG. 5. The kit 500 further includes a second articulation component 120. The second articulation component 120 is shown in greater detail in FIG. 6.

The kit 500 further includes a first fixation component 212. The first fixation component 212 more fully shown in FIG. 7. The kit 500 further includes a second fixation component, for example, component 312. The second fixation component 312 is shown in greater detail in FIG. 9.

The kit 500 may further include a third fixation component 412. The third fixation component 412 is shown in greater detail in FIG. 10.

It should be appreciated that the kit 500 may further include additional articulating components. For example, a third, fourth, or fifth or more articulation components (not shown). Similarly, the kit 500 may include additional fixation components, for example, a fourth fixation component, a fifth fixation component or additional fixation components (not shown).

It should be appreciated that the articulating components may have any suitable shape or size of their articulating surface. Similarly, it should be appreciated that the fixation components have any suitable size and shape of the glenoid surface for proper securement to the scapula. Further, it should be appreciated for the components of the glenoid kit 500 to the properly interchanged, the taper protrusions, for example, protrusions 28 of the articulating component 20, as well as, the tapered protrusion 128 of the second articulating component 120 preferably have identical sizes and shapes. Similarly, the internal taper 226 of the first fixation component, the internal taper 326 of the second fixation component as well as the internal taper 426 of the third fixation component 412 have similar sizes and shapes. Further the internal fixation component 226, 326, and 426 are preferably designed to matingly fitted the external components 28 and 128 of the articulating components 20 and 120.

Figure 12:
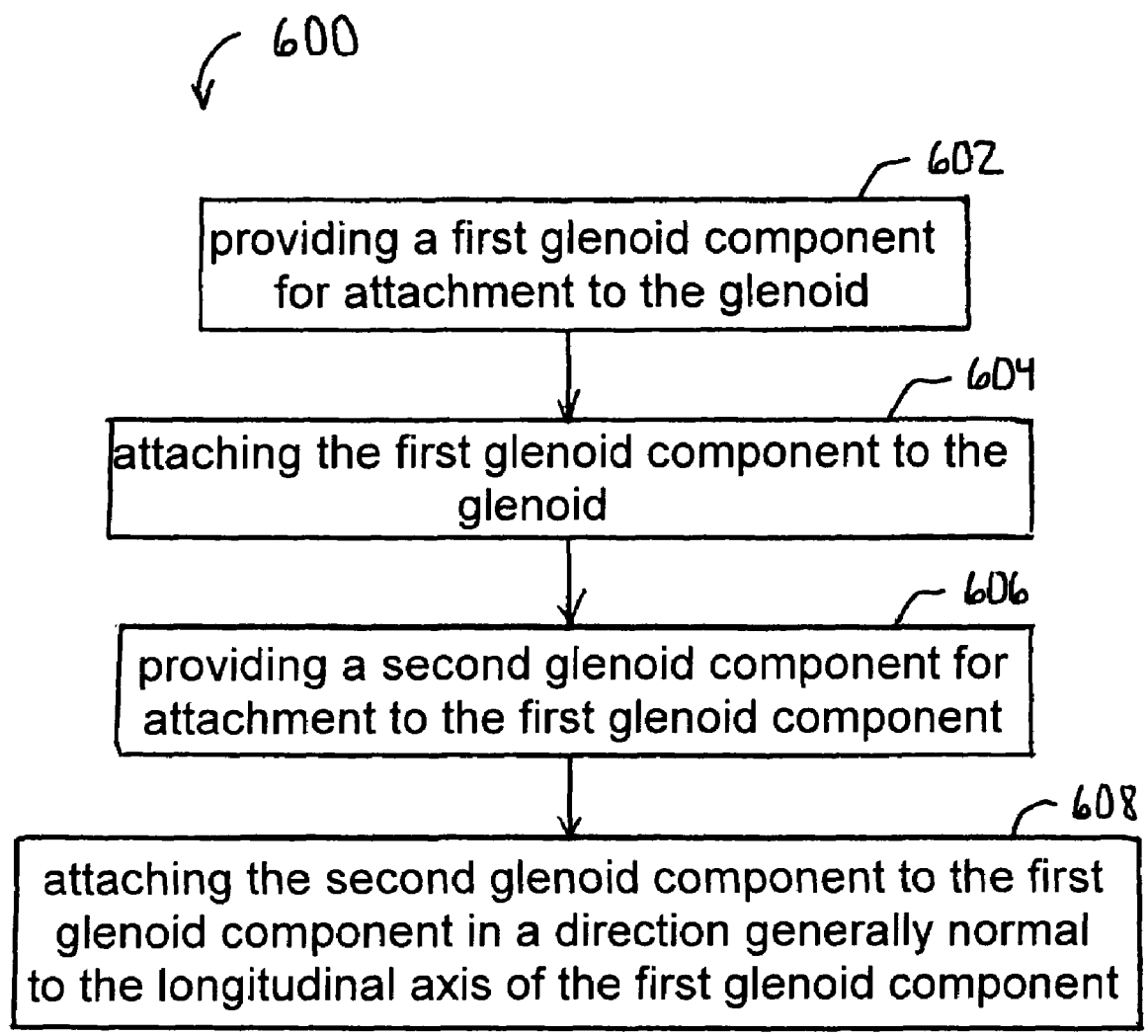
FIG. 12 is a flow chart of a method for performing total shoulder arthroplasty in accordance with another embodiment of the present invention.

Referring now to FIG. 12, another embodiment of the present invention is shown as method 600 for performing shoulder surgery. The method 600 further includes a first step 602 of providing a first glenoid component for attachment to the glenoid. The method 600 further includes a second step 604 of attaching the first glenoid component to the glenoid. The method 600 further includes a third step 606 of providing a second glenoid component to attachment to the first glenoid component. The method 600 further includes a fourth step 608 of attaching the second glenoid component to the first glenoid component in the direction generally normal to the longitudinal axis of the first glenoid component.

Although the present invention and its advantages have been described in detail, it should be understood that various changes, substitutions, and alterations can be made therein without departing from the spirit and scope of the present invention as defined by the appended claims.

We claim:

1. A glenoid implant assembly comprising:
a first component for fixable attachment to the glenoid fossa of a scapula, said first component defining a generally spherically concave assembly face thereof, said first component further having a bone engaging face opposed to the assembly face, the bone engaging face abutting and being contained within the scapula;
a second component removably secured to said first component, said second component including an assembly face thereof, the assembly face of said second component in close approximation to the assembly face of said first component when said first and second component are secured together, said second component attachable to said first component in a direction generally normal to the assembly faces, said second component including an opposing face opposite the assembly face, the opposing face being generally concave; and
a third component removably securable to said first component, said third component including an assembly face thereof, the assembly face of said third component in close approximation to the assembly face of said first component when said first and third component are secured together, said third component attachable to said first component in a direction generally normal to the assembly faces, said third component including an opposing face opposite the assembly face, the opposing face comprising a spherically convex articulating bearing component;
wherein at least one of said second component and said third component are secured to said first component; and
wherein said first component comprises an augmentation extending distally from a portion of said bone engaging surface of said first component sized and shaped for replacing a void in the scapula caused by abnormal wear of the glenoid fossa.

2. The glenoid implant assembly of claim 1:
wherein said first component includes an attachment feature; and
wherein at least one of said second component and said third component includes an attachment feature, the attachment feature of said first component cooperating with the attachment feature of at least one of said second component and said third component to secure said second component to said first component.

3. The glenoid implant assembly of claim 2, wherein at least one of the attachment feature of said first component and the attachment feature of at least one of said second component and said third component comprises one of a tapered connection, a threaded connection, and an interference connection.

4. The glenoid implant assembly of claim 3:
wherein the attachment feature of said first component and the attachment feature of at least one of said second component and said third component comprise a tapered connection;

wherein one of the attachment features of said first component and the attachment feature of at least one of said second and said third component comprise a male taper; and wherein the other attachment feature of said first component and the attachment feature of at least one of said second component and said third component comprise a female taper.

5. The glenoid implant assembly of claim 4, wherein the tapered connection is a self-locking taper.

6. The glenoid implant assembly of claim 5, where the tapered connection defines an included angle of about less than 19 degrees.

7. The glenoid implant assembly of claim 1, wherein said first component, said second component, and said third component comprise a metal.

8. The glenoid implant assembly of claim 1, wherein first component comprises a feature for securement to the glenoid vault.

9. The glenoid implant assembly of claim 1, wherein at least one of said first component, said second component, and said third component comprises at least one of a metal, a biologic material, a ceramic, an alumina, a zirconia, a carbon fiber material, a composite a porous coating, and a plastic.

10. A glenoid implant assembly comprising:
a first component for fixable attachment to the glenoid fossa of a scapula, said first component defining a generally, spherically concave assembly face and attachment feature thereof, said first component further having a bone engaging face opposed to the assembly face, the bone engaging face abutting and being contained within the scapula;
a second component removably secured to said first component, said second component including an assembly face thereof, said second component defining an attachment feature thereof, the attachment feature of said second component adapted for attaching to the attachment feature of said first component in a direction generally normal to the assembly faces, said second component including an opposing face opposite the assembly face, the opposing face being generally concave;
a third component removably securable to said first component, said third component including an assembly face thereof, the assembly face of said third component in close approximation to the assembly face of said first component when said first and third component are secured together, said third component attachable to said first component in a direction generally normal to the assembly faces, said third component including an opposing face opposite the assembly face, the opposing face comprising a spherically convex articulating bearing component;
wherein at least one of said second component and said third component are secured to said first component;
wherein said first component comprises an augmentation extending distally from a portion of said bone engaging surface of said first component sized and shaped for replacing a void in the scapula caused by abnormal wear of the glenoid fossa.

11. The glenoid implant assembly of claim 10:
wherein the attachment feature of said first component and the attachment feature of at least one of said second component and said third component comprise a tapered connection;

wherein one of the attachment features of said first component and the attachment feature of at least one of said second component and said third component comprise a male taper; and wherein the other attachment feature of said first component and the attachment feature of at least one of said second component and said third component comprise a female taper.

12. The glenoid implant assembly of claim 11, wherein the tapered connection is a self-locking taper.

13. The glenoid implant assembly of claim 12, where the tapered connection defines an included angle of about less than 19 degrees.

14. The glenoid implant assembly of claim 10, wherein said first component, said second component, and said third component comprise a metal.

15. The glenoid implant assembly of claim 10, wherein first component comprises a feature for securement to the glenoid vault.

16. The glenoid implant assembly of claim 10, wherein at least one of said first component, said second component, and said third component comprises at least one of a metal, a biologic material, a ceramic, an alumina, a zirconia, a carbon fiber material, a composite a porous coating, and a plastic.

17. The glenoid implant assembly of claim 10, wherein said second component further comprises an articulation face for cooperation with one of a humeral prosthesis or a natural humerus.

18. A glenoid implant assembly comprising:
a first component for fixable attachment to the glenoid fossa of a scapula, said first component defining a generally spherically convcave assembly face thereof, said first component further having a bone engaging face opposed to the assembly face, the bone engaging face having a generally convex shape and for abutting and being contained within the scapula;
a second component removably secured to said first component, said second component including an assembly face thereof, the assembly face of said second component in close approximation to the assembly face of said first component when said first and second components are secured together said second component attachable to said first component in a direction generally normal to the assembly faces, said second component including an opposing face opposite the assembly face, the opposing face being generally concave;
a third component removably securable to said first component, said third component including an assembly face thereof, the assembly face of said third component in close approximation to the assembly face of said first component when said first and third component are secured together, said third component attachable to said first component in a direction generally normal to the assembly faces, said third component including an opposing face opposite the assembly face, the opposing face comprising a spherically convex articulating bearing component;
wherein at least one of said second component and said third component are secured to said first component;
wherein said first component comprises an augmentation extending distally from a portion of said bone engaging surface of said first component sized and shaped for replacing a void in the scapula caused by abnormal wear of the glenoid fossa.

19. The glenoid implant assembly of claim 18:
wherein said first component includes an attachment feature; and wherein at least one of said second component and said third component includes an attachment feature, the attachment feature of said first component cooperating with the attachment feature of at least one of said second component and said third component to secure said second component to said first component.

20. The glenoid implant assembly of claim 18, wherein the assembly face of said first component has a generally concave shape.

21. The glenoid implant assembly of claim 20:
wherein the attachment feature of said first component and the attachment feature of at least one of said second component and said third component comprise a tapered connection;
wherein one of the attachment features of said first component and the attachment feature of at least one of said second component and said third component comprise a male taper; and
wherein the other attachment feature of said first component and the attachment feature of at least one of said second component and said third component comprise a female taper.

22. The glenoid implant assembly of claim 21, wherein the tapered connection is a self-locking taper.

23. The glenoid implant assembly of claim 22, where the tapered connection defines an included angle of about less than 19 degrees.

24. The glenoid implant assembly of claim 18, wherein said first component, said second component, and said third component comprise a metal.

25. The glenoid implant assembly of claim 18, wherein first component comprises a feature for securement to the glenoid vault.

* * * * *